United States Patent
D'Hooge et al.

(10) Patent No.: US 9,035,268 B2
(45) Date of Patent: May 19, 2015

(54) NON-INVASIVE IN-SITU RADIATION DOSIMETRY

(75) Inventors: Jan D'Hooge, Mechelen (BE); Helge Pfeiffer, Wezemaal (BE); Koen Van Den Abeele, Sinaai (BE); Erik Verboven, Bekkevoort (BE); Emiliano D'Agostino, Mol (BE)

(73) Assignees: KATHOLIEKE UNIVERSITEIT LEUVEN, Leuven (BE); SCK CEN, Brussels (BE)

( * ) Notice: Subject to any disclaimer, the term of this patent is extended or adjusted under 35 U.S.C. 154(b) by 0 days.

(21) Appl. No.: 14/343,112

(22) PCT Filed: Sep. 7, 2012

(86) PCT No.: PCT/EP2012/067539
§ 371 (c)(1),
(2), (4) Date: Mar. 6, 2014

(87) PCT Pub. No.: WO2013/034709
PCT Pub. Date: Mar. 14, 2013

(65) Prior Publication Data
US 2014/0213841 A1  Jul. 31, 2014

(30) Foreign Application Priority Data
Sep. 7, 2011  (GB) .................................. 1115419.2

(51) Int. Cl.
*A61N 5/10* (2006.01)
*A61B 8/08* (2006.01)
(Continued)

(52) U.S. Cl.
CPC .............. *A61N 5/1071* (2013.01); *A61B 8/481* (2013.01); *A61K 9/50* (2013.01); *A61K 9/51* (2013.01); *A61B 8/0833* (2013.01); *A61B 8/483* (2013.01);
(Continued)

(58) Field of Classification Search
CPC ...... G01T 1/02; A61N 5/1048; A61N 5/1071; A61N 5/10
USPC ....................................................... 250/472.1
See application file for complete search history.

(56) References Cited

U.S. PATENT DOCUMENTS 4,309,307 A * 1/1982 Christophorou et al. ..... 252/372
5,236,693 A   8/1993 Lee
(Continued)

FOREIGN PATENT DOCUMENTS

WO   2010073164 A1   7/2010

OTHER PUBLICATIONS

Hoff, "Acoustic Characterization of Contrast Agents for Medical Ultrasound Imaging," Norwegian University of Science and Technology, Apr. 2000, pp. 1-229.
(Continued)

*Primary Examiner* — Marcus Taningco
(74) *Attorney, Agent, or Firm* — Workman Nydegger

(57) ABSTRACT

A system for measuring radiation dose comprises an excitation device adapted for directing an energy wave at a volume of a substance comprising gas-filled microparticles, a detector for detecting a response signal emitted and/or modified from the volume of the substance comprising gas-filled microparticles; and a control unit. The control unit is adapted for calculating a dose of ionizing radiation previously received by the volume of the substance based on the response signal. A method includes measuring a received dose of ionizing radiation and using a contrast agent for non-invasive in-situ dosimetry.

19 Claims, 17 Drawing Sheets

(51) Int. Cl.
- *G01T 1/02* (2006.01)
- *G01T 1/20* (2006.01)
- *A61K 9/50* (2006.01)
- *A61K 9/51* (2006.01)
- *A61K 9/00* (2006.01)
- *A61K 9/10* (2006.01)
- *A61K 49/22* (2006.01)
- *A61N 7/00* (2006.01)

(52) U.S. Cl.
CPC ............... *A61B 8/485* (2013.01); *A61K 9/0019* (2013.01); *A61K 9/10* (2013.01); *A61K 49/223* (2013.01); *A61N 7/00* (2013.01); *G01T 1/023* (2013.01); *G01T 1/2012* (2013.01)

(56) References Cited

U.S. PATENT DOCUMENTS

| | | |
|---|---|---|
| 2004/0236207 A1 | 11/2004 | Widener et al. |
| 2007/0239000 A1* | 10/2007 | Emery et al. ................ 600/437 |
| 2011/0009734 A1* | 1/2011 | Foley et al. ................ 600/411 |
| 2011/0081724 A1 | 4/2011 | Swager et al. |
| 2011/0121188 A1 | 5/2011 | Black et al. |
| 2011/0254842 A1 | 10/2011 | Dmitrieva et al. |

OTHER PUBLICATIONS

International Search Report for corresponding International PCT Application No. PCT/EP2012/067539, mailed Nov. 8, 2012.

Juffermans et al. "Ultrasound and Microbubble-Targeted Delivery of Therapeutic Compounds," Netherlands Heart Journal, Feb. 2009, pp. 82-86, vol. 17, No. 2.

Prager et al., "Three-Dimensional Ultrasound Imaging," Proceedings of the Institution of Mechanical Engineers, Part H: Journal Engineering in Medicine, 2010, pp. 193-223, vol. 224.

Runge, "Contrast Agents: Safety Profile," URL: http://cds.ismrm.org/ismrm-2008/files/Syllabus-69.pdf, 2008, 6 pages.

Singh et al., "Potential Toxicity of Superparamagnetic Iron Oxide Nanoparticles (SPION)," Nano Reviews, Sep. 21, 2010, pp. 1-15.

* cited by examiner (a)

(b)

(a)

(b)

NON-INVASIVE IN-SITU RADIATION DOSIMETRY

FIELD OF THE INVENTION

The invention relates to the field of radiation dosimetry. More specifically it relates to systems and methods for in-situ radiation dosimetry, in particular non-invasive radiation dosimetry.

BACKGROUND OF THE INVENTION

With an estimated 2.9 million new cases (54% occurring in men, 46% in women) and 1.7 million deaths (56% in men, 44% in women) each year, cancer remains a major public health problem in Europe and the rest of the world. An important modality in any therapeutic cancer strategy is the irradiation of the tumor with high energy photons or particles, i.e. radiotherapy. Developments in radiotherapy treatments have brought solutions that allow a more precise delivery of a higher dose to the tumor with fewer side effects to healthy tissues. Among the new techniques, including tomotherapy and cyberknife, both making use of 6 MV photons, charged particle beams, i.e. hadrontherapy, play an increasingly important role, due to its intrinsic high ballistic precision. Hadrontherapy can allow a very high dose to the target volume, while keeping the dose to the surrounding healthy tissues limited.

The advancement of these treatments is thoroughly related to advances in dosimetry, to fully exploit their high tumor conformity. There are several reported cases of accidents in conventional radiotherapy treatments due to malfunctioning of the equipment, or due to staff mishandling, as can be seen on Robert Johnston's database of radiological incidents and related events, http://www.johnstonsarchive.net/nuclear/radevents/index.html.

Unfortunately no on-line in-vivo dosimetry system is systematically in use in the clinical routine nowadays.

Prior art approaches to on-line in-vivo dosimetry, e.g. making use of diodes, MOSFET's, diamond detectors, TLD's or scintillators, perform a dose measurement at the level of the skin while a measurement in-situ, e.g. at the level of the tumor, would be preferable. Furthermore, methods are known in the application field to enable an in-situ dose assessment using implanted or intra-cavities dosimeters. However, such methods imply a degree of invasiveness. For example, US2011/121188 discloses a system which comprises internally positioning single-use MOSFET dosimeters in a patient's body to evaluate the radiation dose delivered during a medical procedure or treatment session, while the related patent application US2004/236207 discloses positioning single-use adhesive dosimeter patches just onto the skin of a patient. Therefore, the dosage of energy that is planned for, often cannot be measured, determined or monitored very accurately, in the tumor itself.

SUMMARY OF THE INVENTION

A need still exists for an improved device and method for efficiently measuring a radiation dose in and around a tumor, during radiotherapy.

It is an object of embodiments of the present invention to provide efficient means and methods for non-invasive radiation dose quantification, in-situ.

The above objective is accomplished by a method and device according to embodiments of the present invention.

In a first aspect the present invention provides systems for measuring radiation dose. The system comprises an excitation device adapted for directing an energy wave at a volume of a substance comprising gas-filled microparticles, a detector for detecting a response signal emitted and/or modified from the volume of the substance comprising gas-filled microparticles, and a control unit, wherein the control unit is adapted for calculating a dose of ionizing radiation previously or simultaneously received by the volume of the substance based on the response signal.

Preferably the gas-filled microparticles may be elastic. The control unit may be adapted for calculating a dose of ionizing radiation received by the volume of the substance, taking into account a measured or detected change of elasticity of the gas-filled microparticles. The microparticles may comprise a Young modulus in the range of 0 to 30 GPa, 0 not included, more specifically in the range of 0 to 15 GPa, 0 not included, for example in the range of 0.01 to 15 GPa. The gas-filled microparticles may be echogenic. In particular embodiments, the gas-filled microparticles may be encapsulated. In particular embodiments, the gas-filled microparticles may be adapted to comprise at least a binding site. In particular embodiments, the gas-filled microparticles may be under suspension.

In embodiments of the present invention the excitation device comprises an ultrasound or electromagnetic (RF) transducer and the detector is adapted for acquiring an ultrasonic or electromagnetic (RF) response signal from the volume of the substance comprising encapsulated gas-filled microparticles.

Preferably the gas-filled microparticles remain intact when receiving a dose of ionizing radiation. They may be destroyed thereafter, for releasing their content. Typically a pressure or energy higher than 60 kPa may be used to obtain the destruction of the microparticles, for example an energy burst of up to 1000 kPa.

In other embodiments of the present invention the control unit is furthermore adapted for determining a spatial distribution, e.g. a planar and/or a volumetric distribution, of the received dose of ionizing radiation. Preferably, the control unit is adapted for calculating, during radiotherapy, a dose of ionizing radiation received by said volume of the substance.

Preferably the control unit is adapted for calculating, during radiotherapy, a dose of ionizing radiation received by a patient having said volume of the substance administered.

In preferred embodiments of the invention the volume of the substance comprising the encapsulated gas-filled microparticles is dispersible. Preferably the encapsulated gas-filled microparticles are encapsulated gas-filled microspheres.

In other preferred embodiments the volume of a substance comprising the gas-filled microparticles, for example encapsulated, is biocompatible.

In alternative embodiments of the invention, the volume of the substance comprising encapsulated gas-filled microparticles is adapted to dissolve, for example after a time in order of minutes. In some embodiments of the invention, the volume of the substance comprising encapsulated gas-filled microparticles is adapted to interact with the dose of ionizing radiation received by said volume of the substance.

In preferred embodiments of the invention the interaction with the dose of ionizing radiation results in a change of physical properties or chemical properties or a combination of physical and chemical properties of the gas-filled microparticles, whereby said change can be irreversible. The control unit may be adapted for calculating a dose of ionizing radiation received by the volume of the substance, taking into account a change of physical properties or chemical properties or a combination of physical and chemical properties of the gas-filled microparticles due to interaction with the dose of ionizing radiation. The physical properties of said encapsulated gas-filled microparticles may comprise one or more properties selected from the group consisting of radius, size distribution, number of particles, shell thickness, shear modulus, shear viscosity, and surface tension. The chemical properties of said encapsulated gas-filled microparticles may comprise one or more properties selected from the group consisting of equilibrium gas pressure, polytrophic gas constant, coefficient of diffusivity in water, permeability through encapsulation, and Ostwald coefficient.

In preferred embodiments of the invention the gas-filled microparticles are functionalized. Preferably the functionalized gas-filled microparticles are chemically bond with a target having a structural integrity. More specifically, the target may be a specific membrane receptor in a biological cellular matrix.

In other embodiments of the invention, the gas-filled microparticles are composed of a shell and a gas core, wherein the shell is formed by a material selected from the group consisting of albumin, galactose, lipid, polymer and combinations thereof; and the gas core is formed by any of air, octafluoropropane, perfluorocarbon, sulfur hexafluoride, or nitrogen.

Preferably the encapsulated gas-filled microparticles remain intact when calculating a dose of ionizing radiation. The excitation device may be adapted for keeping the encapsulated gas-filled microparticles intact when directing the energy wave at the volume of the substance comprising the gas-filled microparticles. Hereto, for instance, the energy of the energy wave directed to the volume by the excitation device may be limited to below a predetermined threshold, the predetermined threshold being such that energies below this threshold do not burst or otherwise destroy the gas-filled microparticles.

In preferred embodiments of the invention the encapsulated gas-filled microparticles further comprise a pharmacon.

In alternative embodiments of the invention, after measuring a dose of ionizing radiation received by the volume comprising the encapsulated gas-filled microparticles, the encapsulated gas-filled microparticles are allowed to burst and deliver the pharmacon. Hereto, a sufficiently high energy burst may be provided to the gas-filled microparticles, for example an energy burst higher than 60 kPa, even up to 1 MPa.

Preferably the gas-filled microparticles are nonradioactive and/or non-luminescent.

Embodiments of the invention provide that the dose of ionizing radiation applied to a patient is smaller than 300 Gy, more specifically smaller than 100 Gy. Preferably the volume of the substance comprising gas-filled microparticles is a medical agent. More specifically said medical agent is preferably selected from a group consisting of contrast agents and therapeutic agents.

In particular embodiments, the control unit is adapted for controlling the set-up and parameters of the detector, e.g. amplitude, frequency and/or waveform.

In a second aspect the present invention provides methods for measuring a received dose of ionizing radiation. The method comprises directing an energy wave at a volume of a substance comprising gas-filled microparticles, whereby said volume of the substance has been previously exposed to ionizing radiation, detecting a response signal from the volume and determining the radiation dose received by the volume during the previously applied ionizing radiation exposure, taking into account the detected response signal.

Preferably detecting a response signal comprises detecting an interaction between the previously applied ionizing radiation and said volume of the substance.

In embodiments of the invention the method further comprises quantifying said detected interaction by analyzing a dispersive response of the volume in function of the received dose of ionizing radiation.

In other embodiments of the invention, analyzing the dispersive response comprises analyzing dispersive characteristics of parameters of said encapsulated gas-filled microparticles in function of the dose of ionizing radiation. Preferably said parameters comprise one or more parameters selected from the group consisting of phase velocity, attenuation and nonlinearity.

In some embodiments the method furthermore includes a time correcting method, the time correcting method comprising directing an energy wave at a volume of the substance comprising functionalized gas-filled microparticles, whereby said volume is not exposed to ionizing radiation; detecting a response signal from the volume; determining a time correction value taking into account said detected response signal; and applying said time correction value to a detected response signal, determined on a volume previously exposed to ionizing radiation.

Preferably directing an energy wave at the volume of the substance comprises emitting an ultrasonic or RF wave and detecting a response signal comprises detecting an ultrasonic or RF response signal.

Preferably determining the radiation dose includes determining a spatial distribution, e.g. a planar and/or a volumetric distribution, of the radiation dose.

In some embodiments of the invention the method furthermore comprises determining, during and/or after radiotherapy, the radiation dose received by said volume of the substance. In particular embodiments of the present invention, real-time determination of received radiation doses may be performed, i.e. during application of the radiation dose.

In alternative embodiments the method furthermore comprises determining, during and/or after radiotherapy, the radiation dose received by a patient having said volume of the substance administered.

Preferably the method is non-invasive. No surgical steps need to be performed to get a radiation dose detector in a patient at the level of the site to be irradiated.

In a third aspect, the present invention provides the use of a volume of a substance for dosimetry, said volume comprising gas-filled microparticles.

In a use according to embodiments of the present invention, the gas-filled microparticles may be encapsulated. Preferably the gas-filled microparticles are functionalized. The gas-filled microparticles may be chemically bond with a target having structural integrity. The target may for example be a specific membrane receptor in a biological cellular matrix.

In a use according to embodiments of the present invention, the volume of the substance may be a medical agent. Preferably the medical agent is selected from a group consisting of contrast agents and therapeutic agents.

In a use according to embodiments of the present invention, the gas-filled microparticles may be composed of a shell and a gas core. The shell may for example be formed by a material selected from the group consisting of albumin, galactose, lipid, polymer and combinations thereof. The gas core may for example be formed by any of air, octafluoropropane, perfluorocarbon, sulfur hexafluoride or nitrogen. In particular embodiments, the gas-filled microparticles may be composed of a gas core encapsulated by a lipid monolayer membrane shell. Preferably the gas comprises air, perfluorocarbon and/ or nitrogen. Preferably the gas-filled microparticles are elastic. The gas-filled microparticles may comprise a Young's modulus in the range of 0 to 30 GPa, 0 not included, more specifically in the range of 0 to 15 GPa, 0 not included, for example in the range of 0.01 to 15 GPa.

In a use according to embodiments of the present invention, the volume is adapted to be used for in-situ dosimetry and/or to monitor a radiation dose applied to a patient. Preferably said monitoring is performed in real-time and/or said monitoring is non-invasive.

In a use according to embodiments of the present invention, the gas-filled microparticles may be echogenic.

In a use according to embodiments of the present invention, the gas-filled microparticles may be adapted to comprise at least a binding site.

In a use according to embodiments of the present invention, the gas-filled microparticles may be under suspension.

In a use according to embodiments of the present invention, the gas-filled microparticles may be adapted to remain intact when receiving and/or calculating a dose of ionizing radiation.

In a use according to embodiments of the present invention, said volume of the substance comprising encapsulated gas-filled microparticles may be dispersible.

In a use according to embodiments of the present invention, said encapsulated gas-filled microparticles may be encapsulated gas-filled microspheres.

In a use according to embodiments of the present invention, the volume of the substance comprising encapsulated gas-filled microparticles may be biocompatible.

In a use according to embodiments of the present invention, said volume of the substance comprising encapsulated gas-filled microparticles may be adapted to dissolve after a time in order of minutes.

In a use according to embodiments of the present invention, said volume of the substance comprising encapsulated gas-filled microparticles may be adapted to interact with the dose of ionizing radiation received by said volume of the substance. Said interaction with the dose of ionizing radiation may result in a change of physical properties or chemical properties or a combination of physical and chemical properties of the gas-filled microparticles. The physical properties of said encapsulated gas-filled microparticles may comprise one or more properties selected from the group consisting of radius, size distribution, number of particles, shell thickness, shear modulus, shear viscosity, and surface tension. The chemical properties of said encapsulated gas-filled microparticles may comprise one or more properties selected from the group consisting of equilibrium gas pressure, polytrophic gas constant, coefficient of diffusivity in water, permeability through encapsulation, and Ostwald coefficient.

In a use according to embodiments of the present invention, the encapsulated gas-filled microparticles may further comprise a pharmacon. In a use according to embodiments of the present invention, the encapsulated gas-filled microparticles may be adapted to burst and deliver the pharmacon after measuring a dose of ionizing radiation received by the volume comprising the encapsulated gas-filled microparticles.

In a use according to embodiments of the present invention, the gas-filled microparticles may be non-radioactive. In a use according to embodiments of the present invention, the gas-filled microparticles may be non-luminescent.

In a fourth aspect, the present invention provides a system for measuring radiation dose. The system comprises an excitation device adapted for directing an energy wave at a contrast agent which comprises dispersed gas-filled microparticles. The system further comprises a detector for detecting a response signal emitted from the contrast agent and a control unit. This control unit is adapted for calculating, based on the response signal, a dose of ionizing radiation previously received by the contrast agent. The control unit may be adapted for controlling an experimental set-up and parameters of a read-out device, such as for example amplitude, frequency and/or waveform.

In a system according to embodiments of the present invention, the excitation device may comprise a dedicated wave source, e.g. a mechanical or electromagnetic wave source, such as for example an ultrasound transducer or electromagnetic (radio-frequency-RF) emitter, and the detector may be adapted for acquiring a response signal, e.g. a mechanical or electromagnetic response signal, such as for example an ultrasonic or electromagnetic (RF) response signal, from the contrast agent.

In a system according to embodiments of the present invention, the control unit may furthermore be adapted for determining a spatial distribution, e.g. a planar and/or a volumetric distribution, of the received dose of ionizing radiation.

In a system according to embodiments of the present invention, the control unit may be furthermore adapted for calculating, during radiotherapy, a dose of ionizing radiation received by a patient having said contrast agent administered.

In a fifth aspect, the present invention provides a method for measuring a received dose of ionizing radiation. The method comprises directing an energy wave at a contrast agent comprising dispersed gas-filled microparticles and previously exposed to ionizing radiation; and detecting a response signal from the contrast agent. The method further comprises determining the radiation dose received by the contrast agent during the ionizing radiation exposure, taking into account the detected response signal.

In a method according to embodiments of the present invention, directing an energy wave may comprise emitting an ultrasonic or electromagnetic (RF) wave and detecting a response signal may comprise detecting an ultrasonic or electromagnetic (RF) response signal.

In a method according to embodiments of the present invention, determining the radiation dose may include determining a spatial distribution, e.g. a planar and/or a volumetric distribution, of the radiation dose.

A method according to embodiments of the present invention may furthermore comprise determining, during radiotherapy, the radiation dose received by a patient having said contrast agent administered.

In a sixth aspect, the present invention provides the use of a contrast agent for non-invasive in-situ dosimetry.

In a use according to embodiments of the present invention, the contrast agent may comprise dispersed gas-filled micro-bubbles.

In a use according to embodiments of the present invention, the gas-filled micro-bubbles may be composed of a gas core encapsulated by a lipid monolayer membrane shell.

In a use according to embodiments of the present invention, the gas may comprise air, perfluorocarbon and/or nitrogen. The gas may also comprise a mixture of gasses.

In a seventh aspect, the present invention provides a computer program product for, if implemented on a control unit, performing a method according to the second or fifth aspect of the present invention.

In an eighth aspect, the present invention provides a data carrier storing a computer program product according to the seventh aspect of the present invention. The term "data carrier" is equal to the terms "carrier medium" or "computer readable medium", and refers to any medium that participates in providing instructions to a processor for execution. Such a medium may take many forms, including but not limited to, non-volatile media, volatile media, and transmission media. Non-volatile media include, for example, optical or magnetic disks, such as a storage device which is part of mass storage. Volatile media include dynamic memory such as RAM. Common forms of computer readable media include, for example, a floppy disk, a flexible disk, a hard disk, magnetic tape, or any other magnetic medium, a CD-ROM, any other optical medium, punch cards, paper tapes, any other physical medium with patterns of holes, a RAM, a PROM, an EPROM, a FLASH-EPROM, any other memory chip or cartridge, a carrier wave as described hereafter, or any other medium from which a computer can read. Various forms of computer readable media may be involved in carrying one or more sequences of one or more instructions to a processor for execution. For example, the instructions may initially be carried on a magnetic disk of a remote computer. The remote computer can load the instructions into its dynamic memory and send the instructions over a telephone line using a modem. A modem local to the computer system can receive the data on the telephone line and use an infrared transmitter to convert the data to an infrared signal. An infrared detector coupled to a bus can receive the data carried in the infra-red signal and place the data on the bus. The bus carries data to main memory, from which a processor retrieves and executes the instructions. The instructions received by main memory may optionally be stored on a storage device either before or after execution by a processor. The instructions can also be transmitted via a carrier wave in a network, such as a LAN, a WAN or the internet. Transmission media can take the form of acoustic or light waves, such as those generated during radio wave and infrared data communications. Transmission media include coaxial cables, copper wire and fibre optics, including the wires that form a bus within a computer.

In a ninth aspect, the present invention provides in transmission of a computer program product according to the seventh aspect of the present invention over a network.

In embodiments of the present invention, different gas-filled micro- or nanoparticles or bubbles, which are preferably biocompatible, can be used to perform in-situ dosimetry in a non-invasive way. The effect of radiation on the particles can additionally be characterized in different radiation fields, going from calibration sources, up to clinical photon and particle fields.

Micro- or nanoparticles or bubbles according to embodiments of the invention may be adapted for injection into living bodies, e.g. for the purpose of ultrasonic echography.

Embodiments of the present invention provide a medium, preferably comprising gas-filled micro- or nanoparticles, for injection into living bodies, e.g. for the purpose of ultrasonic echography and, more particularly, injectable liquid compositions comprising microbubbles of air or physiologically acceptable gases as stable dispersions or suspensions in an aqueous liquid carrier. These compositions may be used as contrast agents in ultrasonic echography to image the inside of blood-stream vessels and other cavities of living beings, e.g. human patients and animals. Other uses, however, are also contemplated as disclosed hereafter.

Embodiments of the invention can also comprise dry compositions which, upon admixing with an aqueous carrier liquid, will preferably generate the foregoing sterile suspension of microbubbles thereafter usable as contrast agent for ultrasonic echography and other purposes.

It is well known that microbodies like microspheres or microglobules of air or a gas, e.g. microbubbles or microballoons, suspended in a liquid are exceptionally efficient ultrasound reflectors for echography. In this disclosure the term of "micro- or nanobubble" specifically designates air or gas globules in suspension in a liquid which generally results from the introduction therein of air or a gas in divided form, the liquid preferably also containing surfactants or tensides to control the surface properties thereof and the stability of the bubbles. More specifically, one may consider that the internal volume of the microbubbles is limited by the gas/liquid interface, or in other words, the microbubbles according to embodiments of the invention are only bounded by a rather evanescent envelope involving the molecules of the liquid and surfactant loosely bound at the gas to liquid junction boundary.

Another advantage of the bubbles according to embodiments of the invention versus the microcapsules of the prior art surrounded by a rigid but breakable membrane, like for instance glass, which may irreversibly fracture under stress is that when the present suspensions are subject to sudden pressure changes, the present bubbles will momentarily contract elastically and then resume their original shape when the pressure is released. This is important in clinical practice when the microbubbles are for instance pumped through the heart and therefore are exposed to alternating pressure pulses.

The bubble suspensions of the present invention are also useful in other medical/diagnostic applications where it is desirable to target the stabilized microbubbles to specific sites in the body following their injection, for instance to thrombi present in blood vessels, to atherosclerotic lesions (plaques) in arteries, to tumor cells, as well as for the diagnosis of altered surfaces of body cavities, e.g. ulceration sites in the stomach or tumors of the bladder. For this, one can bind monoclonal antibodies tailored by genetic engineering, antibody fragments or polypeptides designed to mimic antibodies, bioadhesive polymers, lectins and other site-recognizing molecules to the surfactant layer stabilizing the microbubbles.

It is an advantage of embodiments according to the present invention that radiation dose absorbed in matter may be quantified.

It is an advantage of embodiments according to the present invention that a spatial distribution of radiation dose absorbed in matter may be quantified.

It is an advantage of embodiments according to the present invention that a temporal evolution of radiation dose absorbed in matter may be monitored, i.e. sampled at multiple moments during radiation exposure.

It is an advantage of embodiments according to the present invention that a spatial distribution of radiation dose absorbed in matter may be quantified non-destructively.

It is an advantage of embodiments according to the present invention that radiation dose received by a patient may be quantified.

It is an advantage of embodiments according to the present invention that radiation dose received by a patient in a predetermined volume of interest, e.g. a tumor site, may be quantified. In addition, it is advantage of embodiments according to the present invention that a homogeneous tumor radiation may be achieved, whereby radiotherapy may be applied in a focused way and whereby an adaptive radiation planning can be enabled.

It is an advantage of embodiments of the present invention that a change of material properties of a volume of a substance, e.g. a contrast agent, comprising microspheres, the change of material properties being induced by an interaction between said microspheres and ionizing radiation, may be detected.

In addition, by detecting the effect of the ionizing radiation on the contrast agent comprising said micro- or nanospheres, advantageously no radioactive sources or active sources, like f.i. fluorescent sources or fluorescent probes, need to be introduced or administered in a patient. The encapsulated gas-filled micro- or nanoparticles according to embodiments of the present invention are not radioactive nor luminescently active, like for instance fluorescent contrast agents.

Moreover, most internal or in-situ dosimetry techniques known in the art are based on calculations and not on measurements. The calculations are either based on models (e.g. MIRD formalism) or on patient specific data (e.g. Monte Carlo calculations). Methods according to embodiments of the present invention are based on actual dosimetry measurements at the actual radiation site.

It is an advantage of embodiments according to the present invention that a permanent change of material properties of a contrast agent comprising microspheres induced by an interaction between said microspheres and ionizing radiation may be detected.

It is an advantage of embodiments according to the present invention that a radiation-induced change in elastic and/or electromagnetic properties of currently available Ultrasound Contrast Agents (UCA's) may be detected. In embodiments according to the present invention, when using gas-filled microbubbles, the bubbles can be altered irreversibly during radiation.

It is an advantage of embodiments of the present invention that a change in physico-chemical behaviour of a contrast agent can be modulated by means of radiation, and that a determination of such change can be used for non-invasive in-situ dosimetry.

It is an advantage of embodiments of the present invention that when using encapsulated gas-filled microbubbles for dosimetry purposes, after performing dosimetry measurements one can activate said encapsulated gas-filled microbubbles by for instance applying a high energy wave to the encapsulated gas-filled micro- or nanoparticles, so as to burst the encapsulated gas-filled microbubbles and thus enhance treatment and the effect of ionizing radiation in tumor cells.

The latter, together with the possibility of quantifying the radiation dose at the level of the tumor, in real-time and non-invasively, provides a drastic improvement of a treatment outcome. In addition, an exact quantification of the radiation dose to the tumor can be determined by embodiments of the present invention, avoiding not only over- but also under-dosage. Over-dosage implies higher dose to healthy tissues as well; under-dosage corresponds to sub-optimal tumor irradiation that can result, after months or years, in tumor recurrence.

Furthermore, embodiments of the present invention improve patient safety. Due to the real-time nature of the technology, treatment errors can be detected and corrected as necessary. This will avoid erroneous irradiations due to mishandling and/or incorrect calibrations. In some embodiments, therapy success can be monitored in a real time fashion without the need of an external imaging system to visualize the tumor.

It is an advantage of embodiments of the present invention where the acoustic properties of encapsulated gas-filled microparticles are detected via ultrasonic methods, as for instance compared to MRI methods, that there is a vast difference in cost and portability between the two devices. Ultrasound is very cost-efficient and widely available.

In addition, since microbubbles can generate such strong signal modifications when applying ultra sound according to embodiments of the invention, a lower intravenous dosage of the volume of the substance comprising dispersed gas-filled microparticles may be needed; micrograms of microbubbles may be sufficient, compared to milligrams for other molecular imaging modalities such as MRI contrast agents. Moreover, targeting strategies for microbubbles are versatile and modular. Targeting a new area only entails conjugating a new ligand.

In alternative embodiments of the invention, the gas cores of the microparticles can be composed of air, or heavy gases like perfluorocarbon, or nitrogen. Advantageously, heavy gases are less water-soluble so they are less likely to leak out from the microbubbles to impair echogenicity. Therefore, microbubbles with heavy gas cores according to embodiments of the present invention are likely to last longer in circulation.

It is a further advantage that embodiments of the present invention provide devices and methods for assessing doses to any tissue, including not only tumor tissue but also tissues surrounding a tumor.

It is another advantage of embodiments of the invention that consistent methods can be used for preliminary imaging and for designing a treatment regimen, as well as for a subsequent verification of the correct delivery of the prescribed irradiation to target tissue. This allows for improved treatment planning, including providing guidance for adjusting a suboptimal treatment to assure that proper therapy is received during subsequent treatment.

The invention according to some embodiments also provides for dosimetry images for later patient follow-up and/or epidemiological studies.

Embodiments of the invention advantageously also provide a method for assessing the treatment of other pathological conditions unrelated to oncology for which radiation therapy is employed.

In addition, for the treatment of pathological conditions treated by radiation, embodiments of the present invention can advantageously also be employed to assess radiation doses in vitro to tissue samples such as biopsies.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

DEFINITIONS

The term "in situ" as used herein refers to examining a phenomenon exactly at the place where it occurs (i.e. without moving it to some special medium).

The term "in vitro" as used herein refers to using components of an organism that have been isolated from their usual biological context in order to permit a more detailed or more convenient analysis than can be done with whole organisms.

The term "real-time" as used herein refers to the observation that the analyzed (input) and generated (output) samples can be processed (or generated) continuously in the time it takes to input and output the same set of samples, independent of the processing delay.

The term "tissue" as used herein is generic and includes tissues comprising organs and surrounding cell groupings.

The term "elastic" as used herein refers to a physical property of a material, whereby the material returns to its original shape after stress is caused. More specifically the term refers to materials with a Young's or E-modulus between 0 and 30 GPa, 0 not being included, more specifically between 0 and 15 GPa, 0 not being included.

The term "echogenic" as used herein refers to the ability to bounce an echo, e.g. return a signal in ultrasound examinations. When an ultrasound signal is used with encapsulated gas-filled microparticles the signal can be increased. This is because microparticles such as microbubbles have a high degree of echogenicity. When gas bubbles are caught in an ultrasonic frequency field, they compress, oscillate, and reflect a characteristic echo- this generates the strong and unique sonogram in contrast-enhanced ultrasound.

Figure 1:
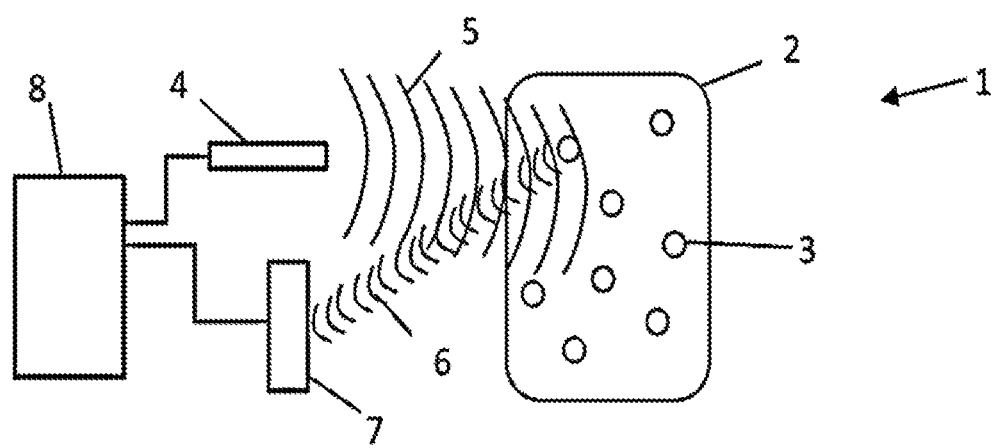
FIG. 1 shows a schematic overview of a system according to embodiments of a first aspect of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

In the context of the present invention, dosimetry relates to determination of an amount of received radiation, e.g. radiation energy, more particularly received ionizing radiation, e.g. radiation energy. In the context of the present invention, ionizing radiation is restricted to radiation capable of ionization in a human or animal body, comprising charged particles such as electrons, protons, pions, nuclei, etc. and/or uncharged particles such as neutrons and photons in the X- and γ-ray energy range.

The present invention relates to systems and methods for determining radiation dose quantities in matter. More specifically, the system may enable determination of absorbed energy in matter, e.g. the absorbed energy per unit mass, $D(r)=d\bar{\epsilon}/dm$, with $\epsilon$ the imparted energy and m the mass, centred at point r. Such dose is measured in Gray (Gy), which is equal to J/kg. This is a local physical property, i.e. defined at individual points. For macroscopic effects, an average absorbed dose may be a more workable property, e.g. $D=\Sigma\bar{\epsilon_i}/\Delta m$, for example such an average value can be assessed for an object of interest, e.g. a biological tissue or an organ. Further derived quantities which may be provided by a system according to the first aspect of the present invention may be the dose rate $\dot{D}$, which is the time derivative of the absorbed dose, and/or Kerma K, which is the kinetic energy transferred by uncharged particles to charged particles that are released by them. A common quantity is for example air-Kerma or Kerma in air, i.e. such kinetic energy released in a volume element of air.

In predicting biological consequences, these physical dose quantities are only a first step. Protection dose quantities try to fill in the blanks by taking into account the detriment on healthy organs or tissue types. The condition that one puts on these dose quantities is that they are practical and reliable. This implies that complex relationships between radiation and risks are strongly simplified. Two important protection dose quantities are the equivalent dose and the effective dose. The equivalent dose H measures the biological effect of an absorbed dose on one organ or tissue type and is the result of a multiplication of the absorbed dose D with a radiation weighting factor (radiation quality factor) $w_R$ so that $H=w_R D$. The radiation weighting factor takes into account the fact that the biological effect is dependent on the radiation type, for example: alpha radiation is 20 times more damaging than photon radiation. The effective dose introduces a way to compare the different exposures on one risk scale. Since different organs or tissue types appear to behave differently under a same equivalent dose, a tissue weighting factor $w_T$ was devised, so that the effective dose reads $E=\Sigma w_T \Sigma w_R D_{T,R}$. It is to be noted that the effective dose still does not take into account factors like age, weight and gender of a body, for example of a patient, being irradiated with ionizing radiation. Both the equivalent dose and the effective dose are expressed in units of Sievert (Sv).

In practice it is not possible to directly measure the protection dose quantities since they are defined in the human body. Therefore a third category of quantities was introduced: operational dose quantities. The goal of these quantities is to be easily measurable and to be a good representation of the protection dose quantities. Two of these quantities are the personal dose equivalent $H_p(d)$ and the ambient dose equivalent $H^*(d)$.

Referring to FIG. 1, the present invention relates in a first aspect to a system 1 for measuring radiation dose. In this system a volume of a substance, e.g. a contrast agent 2, comprising dispersed gas-filled microparticles 3, e.g. microspheres, is used and exposed to the radiation dose. This exposure of the volume of the substance is performed before performing a measurement method for determining a received radiation does according to embodiments of the present invention. The act of exposing the volume of the substance comprising the dispersed gas-filled microparticles 3 does not form part of any of the embodiments of the present invention. In the following, as an example for the volume of the substance, reference is made to a contrast agent. This, however, is not intended to be limiting, and where "contrast agent" is written, the broader terminology "volume of a substance" should be understood.

The read-out device of the system (comprising a control unit 8, sender 4 and receiver 7) analyzes particular characteristics of the contrast agents solution which can be used to infer the radiation dose.

Systems 1 according to embodiments of the first aspect of the present invention comprise an excitation device 4 for directing an energy wave 5 to the contrast agent 2 and a detector 7 for acquiring a response signal 6 emitted from the contrast agent 2, e.g. produced by the interaction of the energy wave 5 with the dispersed gas-filled microparticles 3, e.g. microspheres. For example, the system 1 may comprise as an excitation device 4/detector 7 assembly at least one ultrasound transducer, e.g. as part of an ultrasound unit adapted for emitting as an energy wave 5 an ultrasound wave directed at the contrast agent 2 and for subsequently detecting an ultrasonic response signal 6 from the contrast agent 2. Alternative read-out devices may be based on the interaction of contrast agents with electromagnetic (RF) waves.

Systems 1 according to embodiments of the first aspect of the present invention may furthermore comprise a control unit 8 adapted for controlling the experimental set-up and parameters of the read-out device (basically amplitude, frequency and/or waveform), and for calculating, based on the response signal 6, a radiation dose received by the contrast agent 2, hence by the previously irradiated body or a portion thereof. This radiation dose may comprise any known radiation-related quantity as known to a person skilled in the art, such as, as discussed hereabove, absorbed dose in mass, Kerma, equivalent dose, effective dose and/or operational dose quantities. The amount of radiation, e.g. radiation dose, used in radiation therapy is measured in gray (Gy), and varies depending on the type and stage of cancer being treated. For curative cases, the typical dose for a solid epithelial tumor ranges from 60 to 80 Gy, while lymphoma tumors are treated with 20 to 40 Gy. Preventative (adjuvant) doses are typically around 45-60 Gy in 1.8-2 Gy fractions (for Breast, Head and Neck cancers respectively). Many other factors can be considered by radiation oncologists when selecting a dose, including, but not limited thereto, whether the patient is receiving chemotherapy, whether radiation therapy is being administered before or after surgery, and the degree of success of surgery.

The control unit may refer to any device or portion of a device that processes electronic data, e.g. from registers and/or memory, to transform that electronic data into other electronic data that may for example be stored in registers and/or memory. A control unit may include one or more processors. Such control unit 8 may comprise a computer system, a dedicated integrated programmable unit or may be provided in an integrated system for collecting data from response signals obtained after excitation of a contrast agent 2 by an energy wave 5, e.g. by means of an ultrasound or electromagnetic transmission/reception unit. The control unit 8 may furthermore be adapted for determining a spatial distribution, e.g. a planar and/or a volumetric distribution, of the previously received radiation dose. In embodiments in which the control unit 8 is so adapted, it may be advantageous to adapt the contrast agent 2 in order to restrict mobility of the dispersed microparticles 3, e.g. by using a contrast agent in a gel emulsion, or by using a targeted contrast agent, e.g. in liquid state, in which the microparticles 3 may chemically bond with a target having structural integrity, e.g. specific membrane receptors in a biological cellular matrix. Calculating the radiation dose may comprise application, e.g. fitting, of a predetermined model characterizing the dose-dependence of quantities related to the response signal 6 for the microparticles 3, e.g. microspheres, comprised in the contrast agent 2. Calculating the radiation dose may furthermore comprise compensating for time-dependent factors relating to interaction of the contrast agent 2 with the energy wave 5 or with the surrounding medium.

In particular embodiments of the first aspect of the present invention, the contrast agent 2 may be adapted for introduction into a biological system, e.g. by perfusion and/or diffusion into a plant, animal or human, or in samples obtained therefrom. The contrast agent 2 may furthermore be adapted for in-vivo introduction, e.g. injection into an animal or human subject. Such contrast agent 2 may for example be injected into a patient for non-invasive in-situ radiation dose monitoring, e.g. during radiotherapy. The actual step of in-vivo introduction of the contrast agent 2 does not form part of the present invention.

Figure 2:
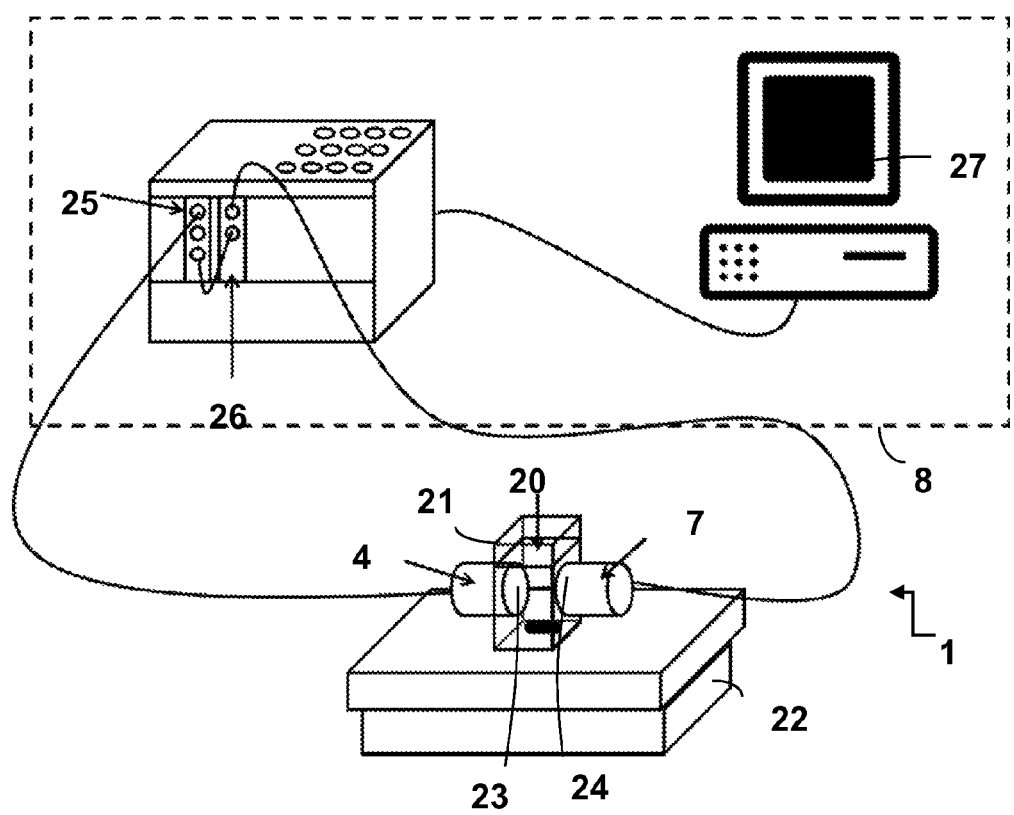
FIG. 2 shows a schematic overview of a system according to an exemplary embodiment of the first aspect of the present invention, using ultrasonic wave emission and detection as a particular example of an energy wave and response signal.

An exemplary embodiment of the system 1 is illustrated by the schematic shown in FIG. 2. It comprises an experimental set-up based on an ultrasonic read-out device, capable of sending and acquiring ultrasonic signals at a wide range of amplitudes and frequencies, and of analyzing the response signals in terms of phase velocity dispersion, attenuation dispersion, and nonlinearity dispersion. The results of this read-out system are used in the examples provided herebelow. In order to determine phase velocity, attenuation and nonlinearity parameters as function of the excitation frequency, this exemplary embodiment comprises a sample of liquid 20, for example placed in a holder 21, e.g. a 2 cm×2 cm×4 cm glass holder. The sample of liquid 20 may be a contrast agent 2 solution comprising microparticles 3, e.g. microspheres or gas-filled micro-bubbles, such as known ultrasound contrast agents, but may also be replaced by a reference sample of pure water or saline solution, e.g. for calibration. Since a few decades now, microscopic bubbles or micro-bubbles are used in contrast agents for ultrasound imaging. These microbubbles may have a substantially spherical shape and may for example be composed of a gas core encapsulated by a lipid monolayer membrane shell. The gas can be any gas, as long as it is not toxic for biological systems, e.g. air or nitrogen. The gas may be a heavier gas, such as perfluorocarbon, in order to avoid diffusion of the gas through the shell, thereby improving the micro-bubble stability. Moreover, the gas may be a mixture of gasses, e.g. argon and methane, in order to obtain a strong response between ionizing radiation and the gas. Ultrasound contrast agents comprising encapsulated gas-filled microbubbles have been known and used by skilled persons in the art since as early as 1990, for instance as disclosed in U.S. Pat. No. 5,236,693. However, the use of such contrast agents for non-invasive in-situ dosimetry has not been found in any of the prior art documents. In addition no document has been found that teaches or hints that encapsulated microbubbles, as in embodiments of the present invention, when intact are sensitive to ionizing radiation, such as gamma rays or high-energy X-rays. Hence the applicant has provided a truly novel and inventive device and method to non-invasively and in-situ and/or in-vivo measure a dose of ionizing radiation.

As discussed earlier, dosimetry of such contrast agents can improve safety and optimize the treatment efficiency when using ionizing radiation on tumors. This need has been addressed by the applicant by proving the existence of some influence of ionizing radiation on the encapsulated gas-filled microbubbles and, in addition, to a point where this influence is measurable and quantifiable acoustically or electromagnetically.

In examples provided further in the present description, a dose-dependent response of micro-bubbles 3 when exposed to ionizing radiation is described. Those examples verify the change of properties of the bubbles 3 under the influence of ionizing radiation by evaluating the alteration of physicochemical properties, e.g. the ultrasonic characteristics, of the microbubble solution. Such a correlation between the change in physico-chemical properties, e.g. ultrasonic response, of the bubbles 3 and the dose imparted to the bubbles 3 may be used in other embodiments of the present invention as an non-invasive in-situ dosimetry system, e.g. for determining radiation dose at a particular location, e.g. the location of a tumor in the body of a patient. As said before, apart from the example of an ultrasonic read-out, other read-out systems based on electromagnetic (RF) waves instead of mechanical waves may be used to evaluate the alteration of properties of the microbubbles upon irradiation, for example a radiofrequency wave suitable for inducing a strong response signal from a contrast agent 2 adapted for such radiofrequency waves. Advantageously, in a preferred embodiment the encapsulated microbubbles behave very similarly to red blood cells (erythrocytes) and when applied in vivo or in situ the encapsulated microbubbles according to embodiments of the present invention dissolve after a time in the order of minutes, depending on the type of encapsulated microbubbles used. In addition, the encapsulated microbubbles of the present invention comprise a safe bio-profile, e.g. a low toxicity as disclosed by Juffermans et al. in Neth Heart J. 2009 Feb. 17 (2): 82-86.

Use of other compounds than microbubbles, as disclosed in the prior art and which may be FDA approved, unfortunately still can have a cytotoxic effect (on the short and/or the longer term), such as for instance is the case with compounds comprising iron oxides or manganese-based contrast agents. Studies by Neenu et al. (in Nano Reviews 2010, 1:5358) and Runda et al. illustrate that in regard to the safety of these agents, the USA package insert for these kinds of compounds indicate that back and leg pain have been reported. More specifically, pain severe enough to cause interruption or discontinuation of the infusion was reported to have occurred in patients.

In the exemplary embodiment illustrated in FIG. 2, the sample of liquid 20 is contained in the holder 21 and may be continuously stirred by a stirrer 22, for example a magnetic stirrer, in order to prevent microbubbles 3 from floating to the surface or sticking to the bottom of the holder 21. The holder 21 may feature an opening 23, 24 on two sides, for example two opposite sides of the holder 21, so that an excitation device 4, e.g. in the form of an emitting transducer, and a detector 7, e.g. in the form of a receiving transducer, may be placed in operational contact with the liquid 20. The distance between emitter and detector may range from 1 to 2 cm. These emitting and receiving transducers 4, 7 may operate at a suitable operation frequency, e.g. a high frequency in the range between 0.1 MHz and 40 MHz, more specifically in the range between 0.5 MHz and 20 MHz. The operating part of the excitation device 4 and the detector 7, i.e. the part being in operational contact with the liquid 20, may have any suitable dimensions, for example a diameter in a range between 0.3 cm to 5 cm. In the examples below, measurements were carried out using 10 MHz, 0.5" (1.3 cm) diameter transducers 4 for emission, and 10 MHz, 0.25" (0.6 cm) diameter transducers 7 for detection.

An energy wave 5, for example in the form of an ultrasonic or RF signal, directed by the emitting transducer 4 to the contrast agent 2, may be produced with a waveform generator 25 coupled to the emitting transducer 4, for example a waveform generator 25 controlled by a software interface, e.g. implemented in LabVIEW. Such generated ultrasonic or RF signals may comprise consecutive sinusoidal bursts with frequencies in a pre-determined frequency range, ranging for example from 0.5 MHz (starting frequency) to 20 MHz (ending frequency), at a pre-determined step frequency, e.g. with 250 kHz steps, and with a predetermined number of multiplier cycles, e.g. between 8 to 50 cycles. At each frequency determined by the frequency range, the starting frequency and the step frequency, the burst signal may be sent either directly to the emitting transducer 4 or fed into an intermediate amplifier linked to the emitting transducer 4. The need for an amplifier may be determined on the basis of the nonlinearity parameter reading, as would be clear to a person skilled in the art. The receiving transducer 7, for example mounted with respect to the holder 21 diametrically opposite to the emitting transducer 4, may for example be coupled to a data acquisition card (DAQ) 26 in a computer. This DAQ 26 may record a time signal, for example measuring a pre-determined time period, e.g. 30-200 microseconds in length, with a pre-determined sampling rate, e.g. ranging from 20 MHz to 1 GHz. The received signals may furthermore be processed by taking a pre-determined number of averages, e.g. 16, 32, 64, 128 or 250 averages, and may be stored in a memory, for example a memory forming part of a computer 27, for further analysis.

In a second aspect, the present invention relates to a method for measuring radiation dose. Before applying the method, a contrast agent 2 comprising dispersed gas-filled microspheres 3 is exposed to ionizing radiation, for example, a contrast agent 2 as discussed hereabove in the context of the first aspect of the present invention. This exposing to ionizing radiation may comprise exposure to natural radiation present in the environment, e.g. originating from cosmic radiation and natural radioactive isotopes, for example present in soil, atmosphere and/or building materials. Alternatively or on top thereof, this exposing to ionizing radiation may comprise an exposure to a source for characterizing said source, e.g. for quantifying a radioisotope preparation. Alternatively or on top thereof, this exposing to ionizing radiation may also comprise introducing the contrast agent 2 in a sample for quantifying and/or monitoring of radiation exposure of such sample under controlled or uncontrolled exposure conditions. This exposing to ionizing radiation may particularly comprise injection of the contrast agent 2 into a complex system, e.g. a biological system, such as an animal or human body, to quantify and/or monitor the dose distribution of radiation internally or externally administered to such complex system. Particularly, exposing the contrast agent 2 to ionizing radiation may comprise injecting the contrast agent 2 into a human or animal patient and administering radiation to said patient, in order to characterize a dose-related quantity expressing radiation exposure to said patient or to at least one volume of interest in the patient's body.

The method according to the second aspect of the present invention comprises directing an energy wave 5 to the previously exposed contrast agent 2, and acquiring a response signal 6 from the contrast agent 2. As an alternative to commercially used contrast agents, contrast agents may be developed with a high dedicated sensitivity to ionizing irradiation. The energy wave 5 may be adapted to the contrast agent used, for optimizing read-out characteristics related to the response signal 6, e.g. for optimizing the magnitude of the response signal. In the supplied examples herebelow, the contrast agent 2 is considered to be an ultrasound contrast agent, and the energy wave 5 is an ultrasonic energy wave suitable for inducing a strong response signal for detection, e.g. comprising reflections of the ultrasonic wave on material interfaces in the contrast agent 2. Alternatively, the energy wave may be an electromagnetic (RF) wave, for example a radiofrequency wave suitable for inducing a strong response signal from a contrast agent 2 adapted for such radiofrequency waves. Ideally, contrast agent properties and energy wave characteristics should be adapted to each other, in view of high responsiveness to irradiation and high read-out sensitivity.

The method according to embodiments of the present invention furthermore comprises determining the radiation dose received by the contrast agent 2 during the preceding ionizing radiation exposure, taking into account the detected response signal 6. For example, as illustrated herebelow, this determining of the radiation dose may take into account an ultrasonic response of ultrasound contrast agent microbubbles 3, e.g. ultrasonic properties such as phase velocity, attenuation and/or nonlinearity dispersion, and a predetermined dose-dependent characterization of such ultrasonic properties. Alternatively, determining of the radiation dose may take into account an electromagnetic, e.g. RF, response of contrast agent micro-bubbles 3. Determining of the radiation dose may furthermore comprise determining a spatial distribution, e.g. a planar and/or a volumetric distribution, of the radiation dose.

In embodiments of the invention, a spatial distribution based on voxel responses can be achieved using a 2D ultrasound probe (phased array). The time dependent backscattered signals at individual voxels can be analyzed and compiled to obtain a full 3D image. This advantageously results in that embodiments according to the invention provide a way to measure a received dose of radiation and enables a localization of the radiation site. As a result effective radiation therapy and planning can be performed.

Each line of the ultrasound array can correspond to a 2D image (planar images) and the different planar images together generate a full (3D) image. In embodiments of the invention a 3D ultrasound image can be achieved by using a 2D array of transducer elements in contact with the object to be scanned. This can record 3D data directly by for instance firing and receiving with different combinations of elements. Because dense arrays of 2D transducers are difficult to build, alternative embodiments can also be used, whereby for instance 1D transducer arrays may be used to produce e.g. 2D B-scan images at known locations in 3D space. Alternative embodiments of image acquisition can involve sweeping a 1D transducer array through a known trajectory using a mechanical device. Other embodiments of image acquisition strategies can comprise letting a clinician sweep a 1D transducer array manually across the subject and using for instance some sort of tracking device to measure its trajectory.

At the simplest level, 3D ultrasound advantageously contributes to eliminating operator dependence in the scanning process. In addition, 3D data enable 3D visualization techniques such as volume rendering and surface rendering to be employed as disclosed by Prager et al. in Proc. IMechE Vol. 224 Part H: J. Engineering in Medicine.

Determining the radiation dose may for example comprise determining the radiation dose received by a patient during administering of radiation, taking into account the detected response signal 6.

The determining of the radiation dose may be implemented in a control unit, e.g. a computer, for example the control unit 8 according to embodiments of the first aspect of the present invention.

In a third aspect, the present invention relates to the use of a contrast agent 2 comprising dispersed microparticles 3, e.g. microspheres, for example a contrast agent comprising gas-filled micro-bubbles, for non-invasive in-situ dosimetry.

In a fourth aspect, the invention relates to a computer program product for, if implemented on a control unit 8, performing a method, e.g. controlling and performing a measurement, according to embodiments of the second aspect of the invention.

In a fifth aspect, the present invention relates to a data carrier storing a computer program product according to embodiments of the fourth aspect.

In a sixth aspect, the present invention relates to transmission of a computer program product according to embodiments of the fifth aspect over a transmission medium such as a local or wide area network.

For clarity, aspects of the present invention not intended to be limited thereby, theoretical principles of the present invention may be explained with reference to the design of gas-filled micro-bubble contrast agents. Such micro-bubbles may for example be suitable for functionalization by state-of-the-art techniques in order to be able to specifically target particular cells, e.g. cancer cells, allowing thus radiation dose quantification at a tumor site. The interaction between ionizing radiation, used to treat particular cell types, such as cancer cells, and the micro-bubbles, for example linked to these cell types, e.g. cancer cells, after functionalization, may induce a permanent change in the micro-bubbles. This change can be detected using different physical principles and/or probes, depending on the chosen bubbles design, e.g. by state-of-the-art ultrasound or electromagnetic imaging in the case of gas-filled micro-bubble ultrasound contrast agents (UCA).

Ultrasound contrast agents or targeted molecular agents can be used for therapy. Advantageously, targeted molecular agents lower the energy threshold for cavitation. When microbubbles cavitate they preferably concentrate the ultrasound energy within a certain region. This region can be selected by for instance steering and focusing an energy beam, e.g. an ultrasound beam. Targeted molecular imaging agents, e.g. ultrasound agents, used in embodiments of the present invention, can be used as beacons to detect regions of disease and then to concentrate an energy wave, e.g. ultrasound energy, within the target region. Contrast enhanced ultrasound for instance has applications for e.g. treatment of thrombosis and drug delivery.

In some embodiments of the present invention a drug or a pharmacon can be incorporated into the encapsulated microbubbles or into encapsulated micro- and nanobubbles according to embodiments of the invention. In alternative embodiments nanoparticles, which may be adapted to be injected in a tumor before radiotherapy, can also be incorporated or loaded into the encapsulated micro- and/or nanobubbles according to embodiments of the invention. An example of such nanoparticles are for instance nanoparticles by Nanobiotix. Advantageously, these nanoparticles can locally boost and/or enhance the radiation dose given to the tumor. This incorporation or loading can be done by a variety of different methods.

Target drug delivery with these micro and/or nanobubbles, is preferably most useful for highly active drugs or pharmacons that preferably do not require large payloads of the drug for biological effect. Many chemotherapeutics, proteins, gene-based drugs or pharmacons are sufficiently active for delivery when applying an energy wave, for instance ultrasound, and targeted acoustically or electromagnetically active carriers. The presence of the gas in for instance a gene-filled micro- or nanobubbles, allows ultrasound energy to burst them. A high energetic wave is preferably generated according to embodiments of the present invention after dosimetry has been performed, as for dosimetry the encapsulated gas-filled microparticles need to be intact. This high energetic wave is then used to burst the bubble and to allow its content, e.g. the gene-based drugs to be released and to enter the cells. Accordingly, substantially the same effect can be observed for gas-filled encapsulated comprising proteins or pharmacons. Thus according to embodiments of the invention, a low intensity, e.g. low pressure, energy wave may preferably be used for performing the dose measurement and, in a next step, after the radiation therapy, a high energy or high pressure wave signal may be generated and applied which is high enough to burst and destroy the bubbles and as a result to release a drug or pharmacon encapsulated in the bubbles. The pressure or energy needed to destroy the bubbles depends on the kind of bubbles. Typically a pressure or energy high than 60 kPa may be used, up to 1000 kPa.

Figure 24:
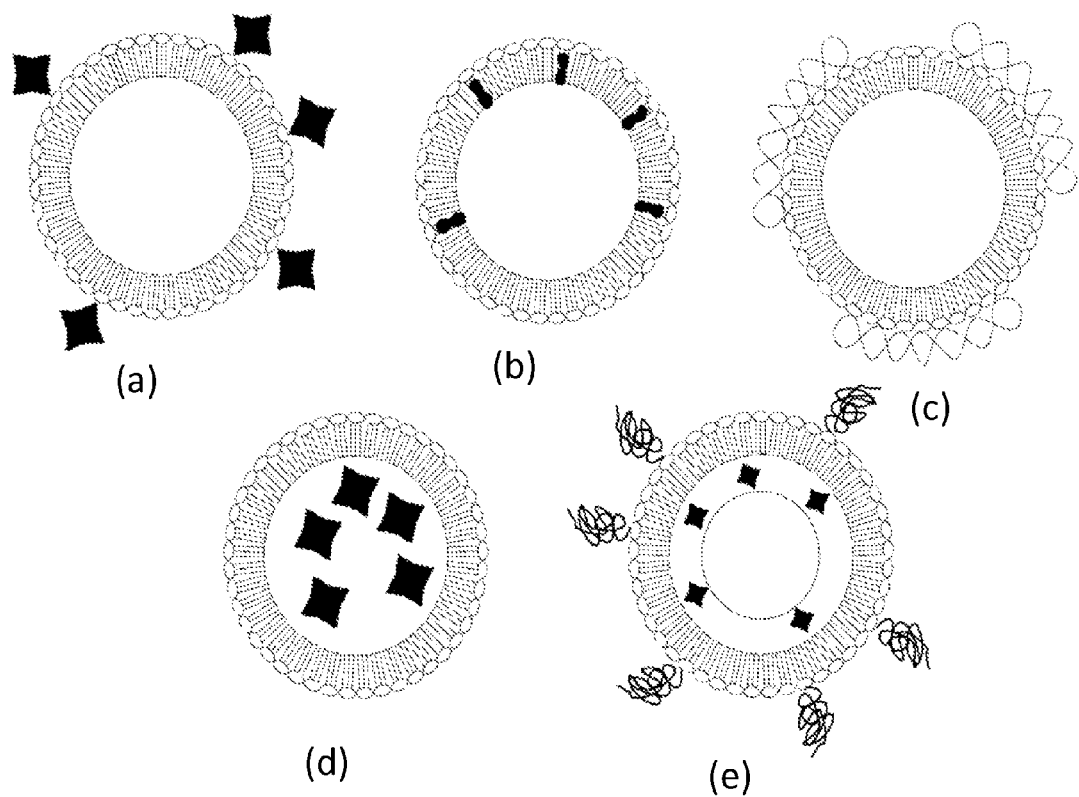
FIGS. 24 (a)-(e) illustrate several embodiments of microbubbles which may be used in embodiments of the present invention, and how such microbubbles can transport drugs.

FIGS. 24(a)-(e) schematically illustrate several embodiments of microbubbles, and how the microbubbles can transport drugs or pharmacons. In FIGS. 24(a)-(e) the stabilizing materials are shown as lipids, but they could be another material, such as polymeric materials. FIG. 24(a) illustrates a drug or pharmacon attached to the membrane surrounding the microbubble. FIG. 24(b) illustrates a drug or pharmacon embedded within the membrane itself. In another embodiment, material such as DNA can be bound non-covalently to the surface of the microbubble, as illustrated in FIG. 24(c). Drug and gas can also be loaded into the interior of the microbubble, as shown in FIG. 24(d). Finally, in FIG. 24(e) hydrophobic drugs can be incorporated into a layer of oily material that forms a film around the microbubble, which is then surrounded by a stabilizing membrane. In this specific embodiment a targeting ligand is incorporated in the membrane, allowing targeted delivery of the drug.

Advantageously, microbubbles and ultrasound techniques used in embodiments of the invention have the potential to being incorporated into other paradigms for molecular images. For example magnetically responsive materials can also be incorporated into microbubbles for MRI. Hybrid forms of imaging incorporating magnetic and optical properties with microbubbles may be exploited to increase sensitivity and therapeutic potential. Such hybrid imaging techniques may improve sensitivity for molecular imaging and our ability to characterize disease.

The effects of ionizing radiation on a bubbly liquid, i.e. a contrast agent 2 comprising micro-bubbles 3, have not, to the inventors' knowledge, been previously studied. The insight that there is an effect of ionizing radiation on a bubbly liquid, lies at the basis of the present invention. The components constituting an ultrasound contrast agent (UCA), namely lipid or protein shells and gas, can be found in other systems and have been studied separately. In order to change the ultrasonic behaviour of an UCA one or more parameters found in the table below need to be altered in such a way that they contribute in a significantly different way to a change in the response signal 6.

| Bubble parameters | |
|---|---|
| Radius | $R_0$ |
| Size distribution | $R_{max}$, $R_{min}$ |
| Number of bubbles | n |
| Shell parameters | |
| Thickness | $d_{s0}$ |
| Shear modulus | $G_S$ |
| Shear viscosity | $\eta_S$ |
| Shear tension | $\gamma$ |
| Content gas parameters | |
| Equilibrium gas pressure | $P_{ge}$ |
| Polytropic gas constant | $\kappa$ |
| Coefficient of diffusivity in water | $k_F$ |
| Permeability through encapsulation | $h_F$ |
| Ostwald coefficient | $L_F$ |

For simplicity, the discussion of theoretical principles will be split into influence of ionizing radiation on the encapsulating material and on the content gas of the microbubbles 3. It is of course understood that interactions may exist, i.e. the gas-filled microbubbles 3 may behave differently than merely predicted based on the combination of its constituents. It is of importance that the effects induced by the two components do not compensate each other, as will be confirmed further herein by experimental data. Moreover, although a variety of shell materials may be used, such as proteins and biopolymers, the present discussion will be limited to lipid shells, as an example only. Such shells are made from the same kind of materials as the lamellar scaffold of biological membranes in cells.

Figure 3:
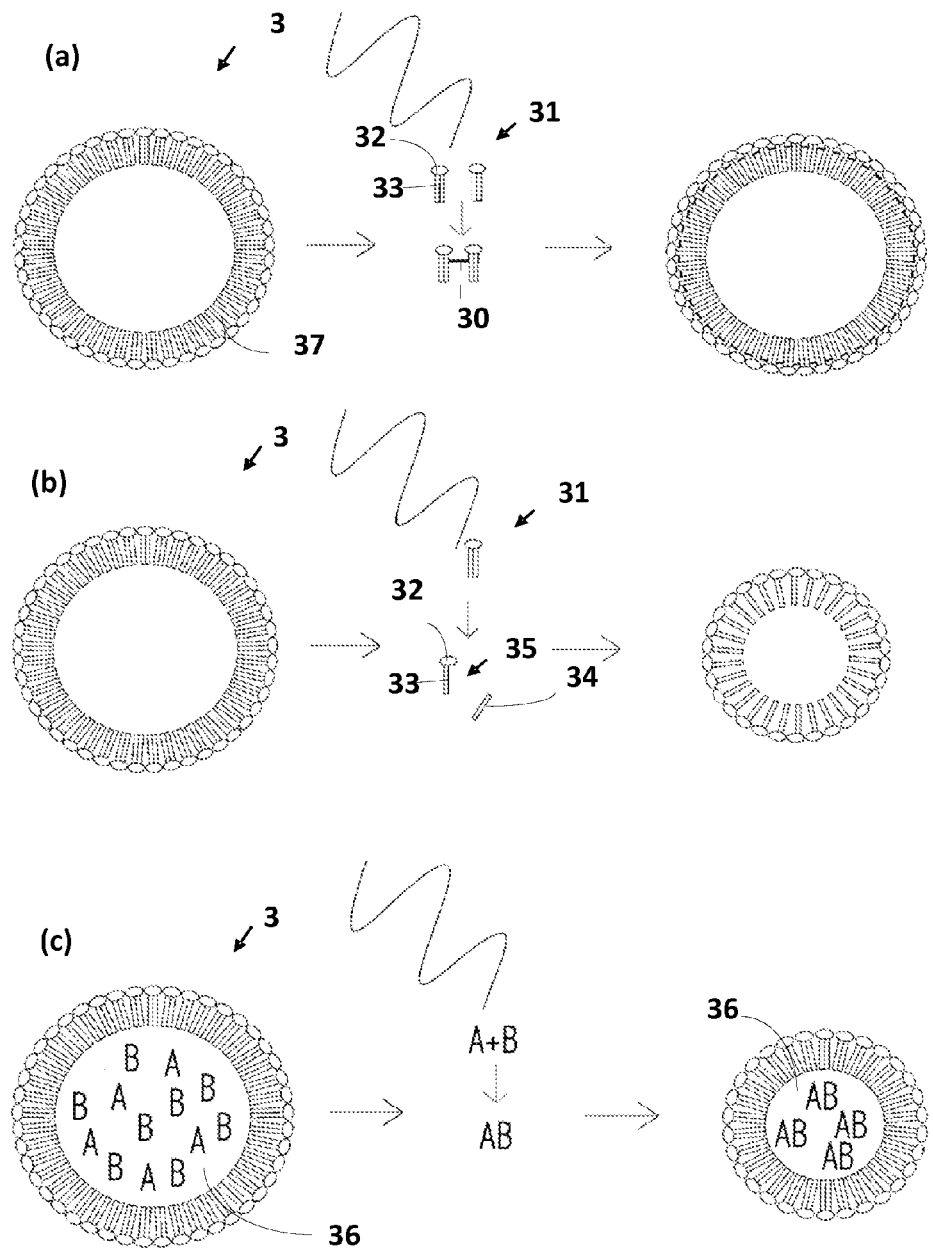
FIG. 3 illustrates how ionizing radiation can interact either with the shell or with the gas core of microbubbles, inducing a change in membrane rigidity and/or curvature of a contrast agent, e.g. an ultrasound contrast agent.

The process of lipid peroxidation is a free radical reaction that occurs with unsaturated lipids. The reason for the fact that the lipids need to be unsaturated lies in the presence of a large number of reactive allyl sites. At these sites a reaction can be initiated by abstraction of a hydrogen atom, starting a chain reaction of free radical reactions. The first step in this cascade is the further reaction of the allyl radical with oxygen forming a hydroperoxide. This hydroperoxide can in turn be oxidized further or act as an oxidizing agent itself. It is now possible that cross-linking reactions between different lipid molecules, such as e.g. phospholipids, take place. Many peroxide bindings can create a firm polymer network. Ionizing radiation can provide the initialization of this process. If lipid peroxidation occurs in the lipids, e.g. phospholipids, in the shell of a microbubble 3 of a UCA 2, the polymerization of the hydrocarbon chains may result in a change of the different properties of the shell. For one, the permeability of the layer may be influenced by an increase in the dielectric constant and by increasing microviscosity. Furthermore a decrease in the shell thickness is a possible consequence of the oxidation. The top illustration (a) in FIG. 3 shows a schematic representation of the polymerization of the phospholipids of an encapsulated microbubble 3. The polymerization is represented as bars 30 between the different phospholipids 31 that are represented by a hydrophilic head 32 and by two hydrocarbon tails 33.

Phospholipids 31 are sensitive to hydrolysis of the ester bonds that are present. During this process fatty acids 34 are released from the phospholipid 31. The remaining part of the molecule has now become a lyso-phospholipid 35 with only one tail 33 left. In the absence of radiation the process can take place both in an acid and in a base environment. The only requirement is the presence of water. In a base environment, the hydrolysis works according to an addition-elimination mechanism. Here a nucleophile hydroxide-ion is added to the carbonyl group, creating a transit state. This addition step is followed by an elimination of the fatty acid 34. The formed carboxylic acid will undergo an acid-base reaction where the equilibrium is towards the right of the reaction. Therefore it proves easier to do a hydrolysis in basic conditions than in acidic conditions. Ionizing radiation could again start up the hydrolysis reaction by splitting water into radicals including a hydroxide radical. If the phospholipids are part of the encapsulating shell 37 of a microbubble 3 of an UCA2, they will change the equilibrium radius of curvature. This can be understood by revisiting the stability conditions for micelles. The type of micelle that may be formed is mainly determined by the molecular structure of the micelle components (usually surfactants, such a phospholipids). First of all the nature of the head group 32 is important. Possible electrostatic repulsion drives the surfactant molecules apart. The hydrophobic tails 33 on the other hand will try to avoid contact with water bringing the surfactant molecules closer together. This will result in an ideal surface A occupied by the head group. Another important factor is the ideal volume V occupied by the tail 33. More repulsion between the tails 33 will result in a larger ideal volume. Now the removal of a hydrocarbon tail 33 can be interpreted as a drop in ideal volume. This drop will cause the phospholipids 31 to move closer together decreasing the equilibrium radius of the microbubble 3. This process can go so far as to decay the bubbles 3 into micelles. Changes in the permeability of the encapsulation can also be expected. The central illustration (b) in FIG. 3 gives a schematic overview of the possible consequences of radio-induced hydrolysis of the phospholipids 31. The freed fatty acids 34 no longer participate in the structure of the shell 37 forcing the remaining molecules to move closer together.

After passing through the encapsulation, the ionizing radiation can interact with the content gas 36. The formation of radicals here, can again affect the encapsulated molecules. Another possible mechanism may influence the core content 36 of the bubble 3. Ionizing radiation can cause the addition reaction of different gas components: A+B→AB . This change in gas content may inspire volume changes. Such volume changes must of course be followed by a change in equilibrium radius. The bottom illustration (c) in FIG. 3 gives an overview of the influence of ionizing radiation on the content gas 36.

Since the proposed models for interaction between ionizing radiation and ultrasound contrast agents 2 may change the physical and chemical properties of the content gas 36 and the encapsulating shell 37, a change in ultrasonic or electromagnetic (RF) behaviour may follow. As for the ultrasonic response analysis, the influence of individual parameter changes on attenuation, phase velocity, non-linearity and/or scattering properties may be evaluated through a parameter study. Concretizing findings thereby obtained to the case of the proposed ionizing radiation—UCA interaction may pose two difficulties.

A first problem relates to the complexity of the reactions. This makes it unlikely that only one parameter will be independently affected as opposed to multiple interacting parameters. For example: polymerization is believed to make the shell 37 more stiff. If this is the case, then both the shear modulus $G_S$ and the shear viscosity $\eta_S$ will be affected. Furthermore it is not unlikely that also the diffusion characteristics are modified. Additionally it cannot be excluded that the different modifications to the parameters work against each other in terms of phase velocity, attenuation and nonlinearity coefficient dispersions, making changes even more challenging to detect.

A second obstacle is the employed ultrasonic model itself. Such a model may rely on some simplifying assumptions. It is not unthinkable that the influence of ionizing radiation is so severe that the system of the bubbly liquid 2 arrives at a situation where some of those assumptions no longer hold. This would render the entire model useless for the situation at hand. Furthermore, the amount of available models for describing bubble dynamics in liquids is enormous.

The enumerated difficulties in finding the correct theoretical predictions for the ultrasonic properties of bubbly liquids, e.g. phase velocity, attenuation and nonlinear coefficient, indicate the need for experimental verification, as provided in various examples set forth herebelow. The first step was to prove the existence of some influence of ionizing radiation on UCA's 2 to the point where it is measurable acoustically. A next step was to link the experimental results to the theoretical propositions.

The methods and systems disclosed herein will further be illustrated using illustrative examples.

Illustrative Examples

In a first illustrative example, a commercially available micro-bubble contrast agent 2, MicroMarker® from Bracco, was used. Different vials of the micro-bubble contrast agent 2 were irradiated using two different radiation qualities: X-rays, obtained from an X-ray tube using a 15 mAs exposure of 250 keV at the calibration facility of SCK•CEN Mol, Belgium, and Co-60 gamma rays, having 1.17 MeV and 1.33 MeV energies, obtained from spent nuclear fuel, at the RITA facility of SCK•CEN Mol, Belgium. At the X-rays tube a dose rate of about 0.75 Gy/min at the distance where the micro-bubble solution was located, was used. In the RITA facility the dose rate was about 10 Gy/min. This very high dose rate enabled imparting a very high dose to the bubbles 3, in a relatively short time, therefore limiting the influence of the spontaneously occurring time changes of the micro-bubbles 3, related to diffusion. The temperature of the microbubble contrast agents 2 was monitored during both types of irradiation, and was observed to remain constant. Therefore the observed radiation-induced changes in ultrasonic dispersion properties of the contrast agents may not be related to radiation-induced temperature rise, and may only be attributed to more direct interaction effects, such as discussed hereinabove.

Figure 4:
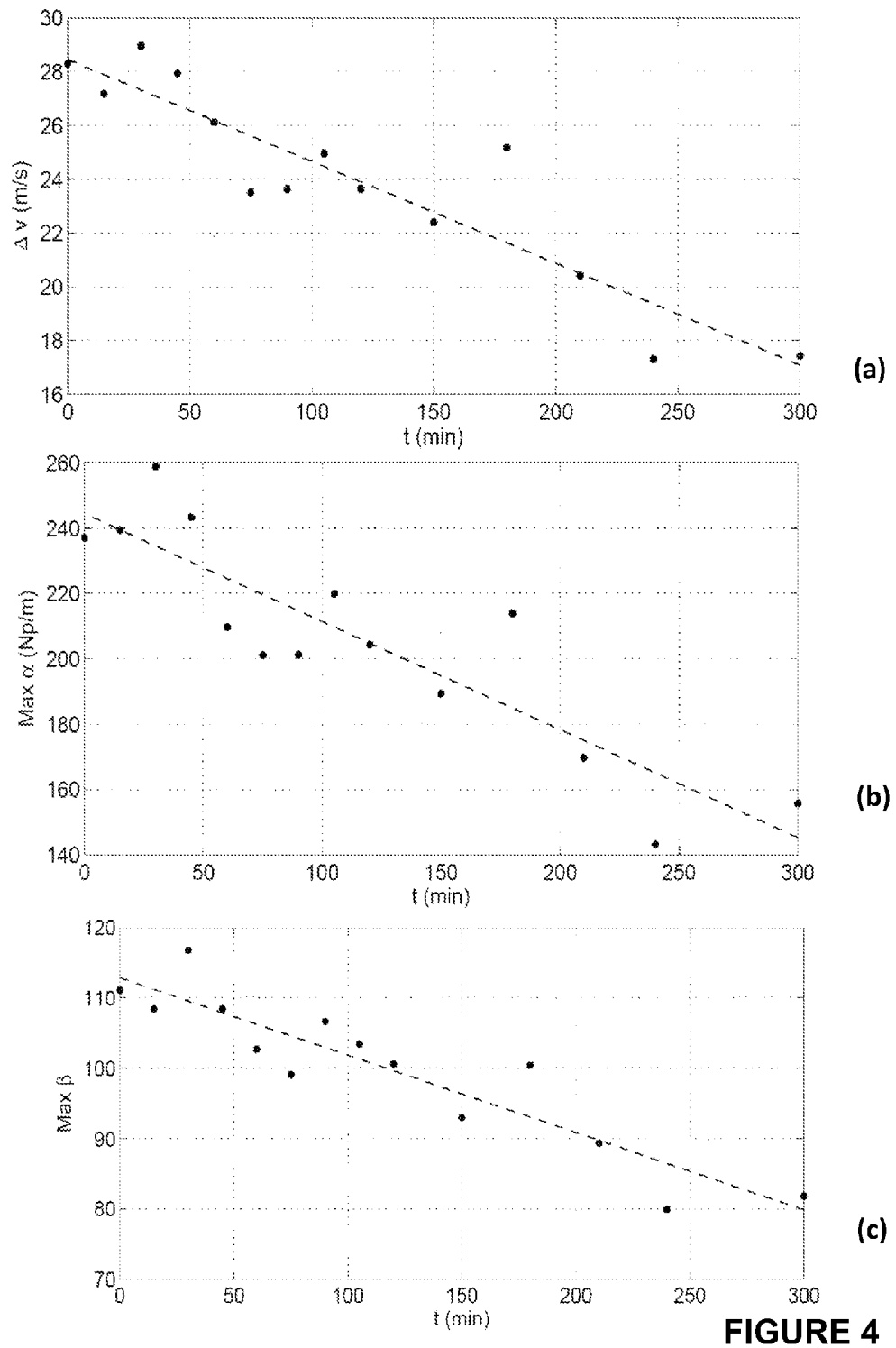
FIG. 4 shows graphs of the time-induced drop of typical dispersion characteristics for the exemplary embodiment using ultrasonic wave emission and detection: (a) phase velocity jump at resonance, (b) attenuation at resonance, and (c) maximum nonlinearity, for non-irradiated micro-bubbles.
Figure 5:
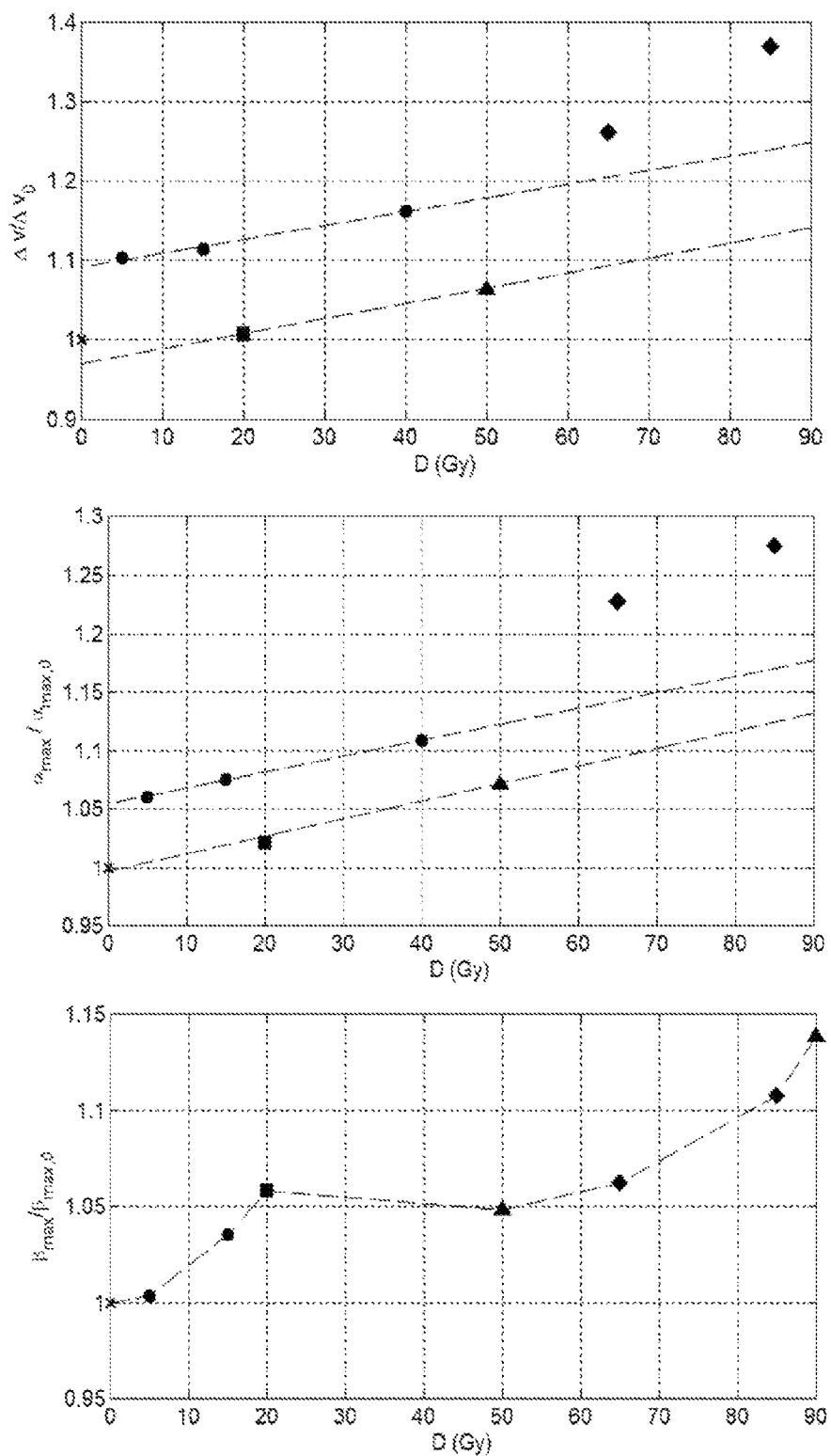
FIG. 5 shows time-corrected graphs of typical dispersion characteristics for the exemplary embodiment using ultrasonic wave emission and detection: (a) phase velocity jump, (b) maximal attenuation and (c) maximal nonlinearity versus absorbed dose, normalized with respect to non-irradiated bubbles (0 Gy).

FIG. 2 is an illustration of the experimental setup used for the ultrasonic dispersion analysis of UCA enriched solutions. The dispersive characteristics of three parameters were analyzed as a function of the dose: ultrasound wave phase velocity, attenuation and nonlinearity. All results were corrected for diffusion by taking into account the evolution over time of non-irradiated bubbles 3. FIG. 4 shows the time evolution of typical dispersion characteristics in the absence of radiation: respectively, from top to bottom, (a) difference between maximal and minimal phase velocity, more specifically a drop in phase velocity jump at resonance in MicroMarker solution (closed vial), (b) maximal attenuation at resonance, more specifically a drop in attenuation in MicroMarker solution (closed vial) and (c) maximum nonlinearity parameter, more specifically a drop in nonlinearity parameter in MicroMarker solution (closed vial). Details of the measurement procedure are explained in the "measurement procedure" section. FIG. 5 shows the results of the typical dispersion characteristics obtained after irradiation of the bubbles 3 for different cumulative dose levels. From top to bottom: (a) normalized jump in phase velocity, (b) normalized maximal attenuation and (c) normalized maximal nonlinear coefficient versus absorbed dose. All data values are time-corrected and shown in normalized form with respect to non-irradiated bubbles (0 Gy). Again, details of the measurement procedure are explained in the "measurement procedure" section. It can clearly be seen that a significant change is induced by ionizing radiation, both for UCA solutions exposed to X-rays (0.75 Gy/min, circles and squares) and to gamma rays (10 Gy/min, triangles and diamonds), on the three ultrasonic dispersion characteristics, phase velocity jump, maximal attenuation and maximal nonlinearity. Moreover, while attenuation and phase velocity show a linear correlation with the dose, the nonlinearity parameter merely displays a quadratic dependence on the absorbed dose.

Contrast Agents

As an example, commercially available MicroMarker (Bracco) microbubbles, a fourth generation UCA, and Sono-Vue microbubbles, a second generation UCA, were tested. The properties of these bubbles can be found in the table herebelow.

| Name | Mean size | Material | $d_S$ | Viscoelastic parameters | gas | manufacturer |
|---|---|---|---|---|---|---|
| SonoVue | 2.5 μm, 90% < 8 μm | Phospho-lipid | 4 nm | $G_S = 46$ MPa, $\eta_S = 0.65$ sPa | $SF_6$ | Bracco (Gen II) |
| Micro-Marker | 2.3-2.9 μm | Phosphor-lipid | 4 nm | NA | N2/perfluo-rocarbon | Bracco (Gen IV) |

Because of the limited stability, investigation on these bubbles needed to be conducted within 4 to 6 hours after reconstitution of a vial of $2 \cdot 10^9$ bubbles/mL for MicroMarker (MM) and a volume fraction $8 \cdot 10^{-3}$ for SonoVue (SV). The bubbles were suspended in a saline solution or in Isoton II, which comprises a phosphate buffer that stabilizes the suspended bubbles, thus providing them with a larger lifespan. Concentration and mean size information were delivered by the manufacturer. However because of the importance of knowing the size distribution for coupling between measurements and simulations, size distributions were determined in this example with the aid of a microscope (see below). The feasibility study of the ultrasonic dispersion characteristics of UCA enriched media after radiation exposure were limited to MicroMarker microbubbles.

Calibration

Figure 6:
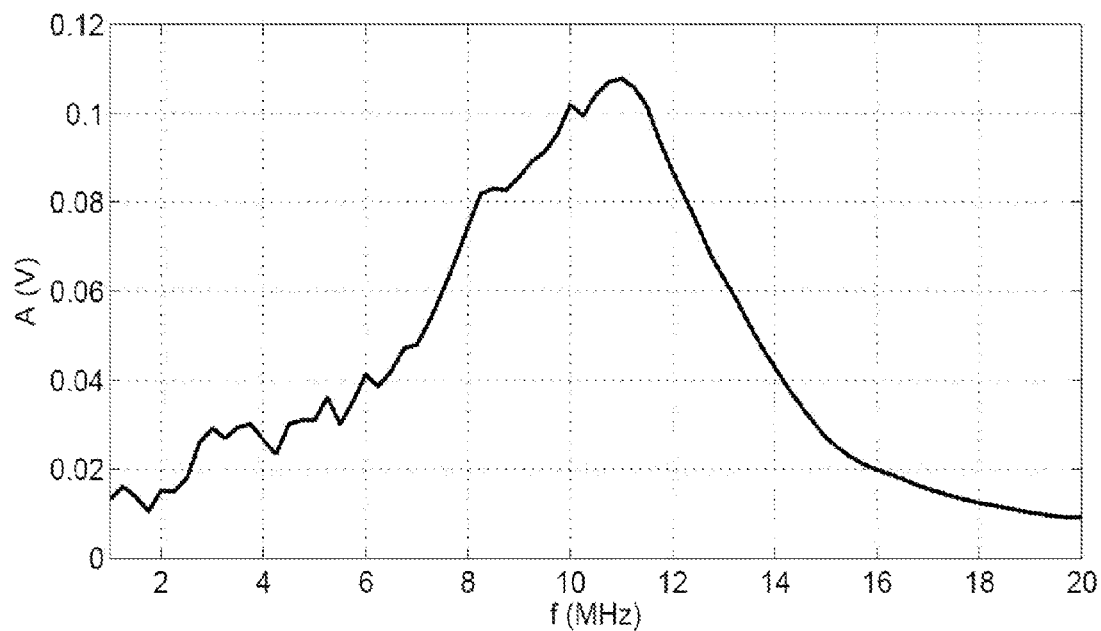
FIG. 6 shows a graph of the spectral output of a 10 MHz transducer at 10 mV input (before amplification) measured by a hydrophone with pre-amplification.

Referring to the examples carried out with an experimental set-up according to the exemplary embodiment illustrated in FIG. 2, it is crucial to limit the energy wave amplitudes to the non-destructive regime for the microbubbles under consideration. Proper knowledge of the output in terms of pressure is required in order to make sure that the pressures received by the bubbles 3 are not much higher than 60 kPa to prevent bubble destruction. Therefore both the emitting transducer 4 and the receiving transducer 7 were calibrated by means of an ONDA, type HGL0400 (1-20 MHz) hydrophone measuring the output in water at a distance of approximately 2 cm (roughly the same distance between the transducers in the glass holder 21). A rough estimate states that 1 mV=0.625 kPa for the hydrophone sensitivity with pre-amplification. The real value, however, is slightly frequency dependent. FIG. 6 shows the resulting graph at 10 mV input (before source amplification), more specifically FIG. 6 shows the calibration curve from a 10 MHz transducer. The amplitude is illustrated versus the frequency. With the output of the hydrophone at 0.1V (with pre-amplification) the peak response of the transducer stays below 62.5 kPa.

Data Analysis

The acquired data resulting from the experimental ultrasonic transmission set-up, can be processed in different ways. In the examples given, the received signals 6 were compared to signals originating from known reference liquids, such as pure water. This method relies on a reference that needs to be measured before the actual bubbly liquid can be measured. The advantage of this method can be found in the fact that temperature fluctuations are factored out. The method only uses the first echo, which has the highest amplitude, from each signal. The disadvantages are the caution that must be taken in removing the reference liquid from the sample holder 21 and the fact that the nonlinear parameter can only be calculated from 1-10 MHz with information on the phase velocity and attenuation from 0.5-20 MHz. Such method is also known as an insert-substitution method. Other methods for the determination of phase velocity, attenuation and non-linearity may include the analysis of multiple echo signals.

This method has the advantage that no reference medium is used. The disadvantage however is the fact that the analysis involves unknown reflection coefficients.

The derivation of the relevant equations for analysis of the measurement results from the insert-substitution method is obtained from the traditional analytical description of nonlinear wave propagation. The derivation starts with an expression for the velocity pattern of an axisymmetric transducer:

$$V_0(r) = \sum_{n=1}^{N} A_n e^{-B_n \left(\frac{r}{a}\right)^2}$$

where a is the effective radius of the transducer, $A_n$ and $B_n$ are the amplitude and the Gaussian complex coefficient of the expansion function respectively. This Gaussian beam expansion can be used as input for the parabolic approximation resulting in the KZK equation for a nonlinear, dissipative and dispersive medium. The nonlinearity is incorporated in this equation through a term proportional to the nonlinearity parameter $\beta_2$; $\rho$ is the density of the liquid and $c_0$ its velocity. Solutions to these equations can be constructed with so-called Green's functions. From the linear superposition principle it follows that the fundamental pressure field can also be expressed as $$p_1(r,z) = \rho c_0 \sum_{n=1}^{N} \frac{A_n}{1 - i\frac{z}{l_d}} e^{\frac{B_n \left(\frac{r}{a}\right)^2}{1 - i\frac{z}{l_d}}} e^{\alpha'_1 z}$$

where $\alpha_1' = \alpha_1 + i(k_1 - nk)$ with $k_1$ the wave number of the fundamental and k a reference wave number, $\alpha_1$ is the attenuation coefficient for the fundamental. $l_d$ is the Rayleigh distance from the transducer. Combination with the solutions to the KZK equations results in an expression for the pressure amplitude of the second harmonic:

$$p_2(r,z) = \frac{\beta_2 k \rho c_0^2}{2} e^{-\alpha'_2 z} \sum_{n=1}^{N} \sum_{m=1}^{M} A_n A_m \int_0^z \frac{e^{-\alpha' z'}}{c_{nm} z'/l_d + d_{nm}} e^{-\left(\frac{r}{a}\right)^2 \frac{a_{nm} z'/l_d + b_{nm}}{c_{nm} z'/l_d + d_{nm}}} dz'$$

where $a_{mn} = i4B_n B_m$, $b_{mn} = -2(B_n + B_m)$, $c_{nm} = 2z/l_d B_n B_m + i(B_n + B_m)$, $d_{nm} = -2 + iz/l_d(B_n + B_m)$ and $\alpha' = 2\alpha'_1 - \alpha'_2$.

On the other hand, ultrasonic wave propagation experiments provide an average pressure over the receiving transducers: $\bar{p}_1$ and $\bar{p}_2$. The above analytical expressions for the fundamental and the second harmonic components allow us to extract the dispersion graphs and the typical dispersion characteristics starting from these experimental data.

Subjected to the following approximations the system can be simplified. First of all it may be assumed that the distance between emitting transducer 4 and receiving transducer 7 is less than 2 cm. Next, the density is considered identical in pure and bubbly liquids. In addition, Isoton II is assumed to be non-attenuating, and the fundamental frequency pressure at the emitter surface is not modified in a bubbly liquid. Finally, diffraction effects are considered to be the same with and without contrast agents.

Given these limitations, the fundamental pressure amplitudes of reference and bubbly liquid can be linked to each other: $\bar{p}_1(z,f) = \bar{p}_{1,ref}(z,f)e^{-\alpha(f)z}$. Under the same conditions, the ratio between the second harmonic pressure amplitudes between reference and contrast mixture reads:

$$\frac{\bar{p}_2(z)}{\bar{p}_{2ref}(z)} = \frac{c^3}{c_0^3} \frac{\frac{\beta(f)}{\beta_{ref}} \frac{1}{z} e^{-2\alpha_1 z} - e^{-\alpha_2 z}}{\alpha_2 - 2\alpha_1}$$

where $\alpha$ is the attenuation coefficient, $c_0$ is the velocity of the reference liquid, z the distance from the emitting transducer, c the frequency dependent velocity of the bubbly liquid.

The phase velocity can be determined by a cross-correlation between the first echoes of the signal received for the reference signal and for the bubbly liquid respectively. This will result in a time difference $\Delta t$ that can be used to determine the phase velocity as follows $$c = \frac{z}{\frac{z}{c_0} + \Delta t}.$$

The dispersion of the phase velocity is evidenced by analyzing the cross-correlation while varying the frequency of excitation over a broad range of frequencies.

From the link between the fundamental pressure of the reference liquid and after bubble injection the frequency dependent attenuation is given by:

$$\alpha(f) = \frac{1}{z}\ln\left(\frac{\bar{p}_{1,ref}}{\bar{p}_1}\right) = \frac{1}{z}\ln(a(f))$$

Here the advantage of the reference method becomes clear. Although the equation still includes the pressure amplitudes of the signal instead of the measured voltage amplitudes, a calibration is not required, since it is only the ratio of the amplitudes that is important. It can be readily understood that the ratio between the voltage amplitudes will yield the same result as the ratio between the pressure amplitudes.

Finally, The nonlinear parameter can be directly calculated from the ratio between itself and the nonlinearity parameter of the reference liquid that is given as:

$$\frac{\beta(f)}{\beta_{ref}} = \frac{\bar{p}_2}{\bar{p}_{2ref}} \frac{c_0^3}{c^3} z \frac{\alpha_2 - 2\alpha_1}{-e^{-\alpha_2 z}}$$

With the aid of the measured phase velocity dispersion and the expression derived for the attenuation that can be written as $\alpha_1 = \ln(a(f))/z$ for the fundamental frequency and $\alpha_2 = \ln(a(2f))/z$ for twice the fundamental frequency, the frequency dependent nonlinear parameter for a UCA can be written down as:

$$\frac{\beta(f)}{\beta_{ref}} = \frac{\bar{p}_2}{\bar{p}_{2ref}} \frac{c_0^3}{c^3} \frac{\ln(a(2f)) - 2\ln(a(f))}{\frac{1}{a^2(f)} - \frac{1}{a(2f)}}$$

where it can be noted that in order to obtain the nonlinearity parameter at frequency f, the attenuation needs to be known at frequency 2f.

Measuring Size Distributions

Bubble size distributions can be determined in different ways. The easiest way is to look up the distribution in previous literature studies. For SonoVue, which has already been approved for human use, the size distribution is well documented. For MicroMarker this is not the case and therefore the size distribution needs to be actually measured. The most common practice is to use a Coulter Multisizer or a Coulter Counter. These devices rely on what is known as the Coulter principle. An alternative method is a microscopical investigation. The procedure here is to fix a few microliters of the bubble solution on a microscope glass. The solution is then put under a predetermined magnification, e.g. a 40× or 100× magnification, and pictures of a predetermined number of different locations, e.g. 5 to 12 different locations, on the glass are taken. These pictures are fed into programs such as for example HCImage or ImageJ where the user, assisted by the program, selects the bubbles to be measured. The advantage of this technique is the availability of microscopes in virtually every laboratory. The disadvantages include the manual processing of the images, the transparency of the bubbles, the impossibility to measure the smallest bubbles and the large uncertainties on the measured diameters.

Figure 7:
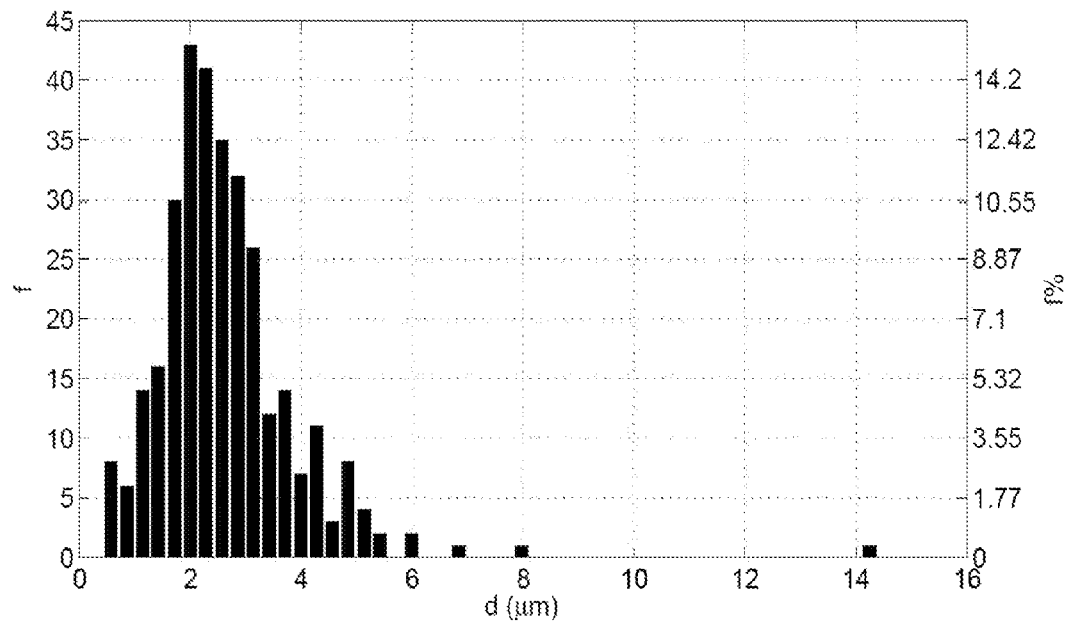
FIG. 7 shows the size distribution of MicroMarker microbubbles as determined by analyzing microscopic images.

In the histogram of FIG. 7, the diameter distribution of MicroMarker contrast agents (2 million bubbles/ml) is shown, for example as determined by analysis of microscopic images. The mean diameter is about 2.3 μm, which is in agreement with the mean diameter size as published by Bracco. Virtually all bubbles are smaller than 10 micrometer which is crucial for passage through the narrowest blood vessels in the body.

In order to use this distribution it will need to be fitted to provide a smooth distribution curve that can be compared to simulations on one hand and to distributions calculated from experimental results on the other hand. It is clear that the rough determination of size distribution will make it very difficult to detect small changes caused by either diffusion or ionizing radiation, so that one will have to rely on the distribution provided by a multiparameter fit. It is also important noting that this distribution was determined immediately after drawing the solution from the vial.

Measurement Procedure without Irradiation

This section presents a step by step guide to ensure reproducible results of experiments and insert-substitution analysis on ultrasonic contrast agents without irradiations. In the following, the term "single measurement" comprises the recording of the response signals in the frequency range 0.5-20 MHz in steps of 0.25 MHz. When compared to the set of reference signals, each single measurement allows a determination of the experimental phase velocity, attenuation and nonlinearity dispersion relations.

1. The sample holder 21 is filled with a predetermined amount of a reference liquid such as distilled water (e.g. 15 ml). An energy wave 5 is emitted to the sample in the sample holder 21, and a response signal 6 is determined. A single measurement is taken without determination of phase velocity, attenuation or nonlinearity parameter.
2. The sample holder 21 is emptied and filled with a predetermined amount of diluents such as a saline solution, e.g. 0.9% NaCl in distilled water, such as an Isoton II solution, which contains a phosphate buffer, e.g. 15 ml. A single measurement is taken for the pure saline solution, and the phase velocity, attenuation and nonlinearity dispersion relations are determined by the reference method. Distilled water is taken as reference.
3. A vial of an ultrasonic contrast agent is prepared. As an example, MicroMarker Contrast Agent, comprising a white powder, may be reconstituted by injecting 1 ml of diluents such as Isoton II in the vial. Then the vial is vented and gently agitated for a predetermined time period, for example 1 minute. Afterwards the solution needs to rest for a while, for example ten minutes. At this point the concentration of the solution in the example described is $2.10^9$ microbubbles/ml.
4. A small amount of ultrasonic contrast agent, e.g. MicroMarker solution, is taken from the vial, for example by means of a syringe with needle, and is put into a recipient, for example an Eppendorf tube.
5. From this recipient, e.g. Eppendorf tube, a predetermined volume, e.g. a volume of 30 microliter, is pipetted into the predetermined amount, e.g. 15 ml, of diluent, e.g. Isoton II, in the sample holder 21, resulting, for the example described, in a final concentration of $4.10^6$ microbubbles/ml. A single measurement is taken with the Isoton II measurement (step 2) as reference. Afterwards the sample holder 21 is emptied and cleaned, e.g. washed with distilled water. The sample holder 21 is refilled with a predetermined amount, e.g. 15 ml, of diluent, e.g. Isoton II.
6. Step 4 and 5 may be repeated twice to ensure repeatability and to be able to take averages.

Results: Measurements without Irradiation

In the following examples, actual phase velocity, attenuation and nonlinearity measurements were carried out by use of the reference method. For distilled water, values for the phase velocity and nonlinearity parameter can be found in literature. First pure water was used as a reference to a pure saline solution. Then, saline solution without contrast agents is used as a reference to saline solutions with enrichment of contrast agents. In the experiments, Random Interleaved Sampling (RIS) was employed to achieve a 1 GHz effective sampling rate.

Figure 8:
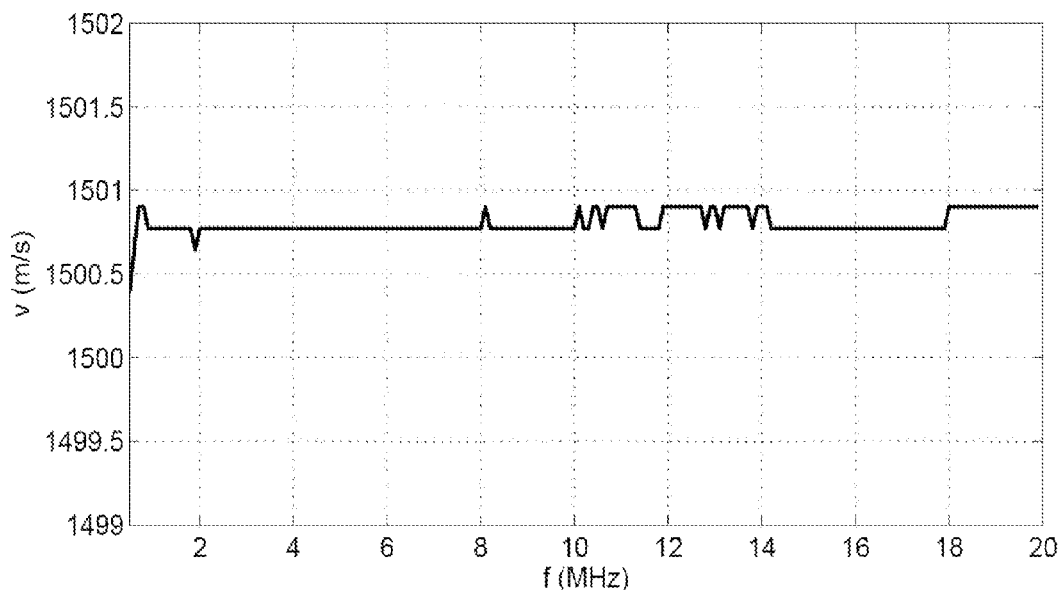
FIG. 8 shows a phase velocity measurement result for pure Isoton II (no dispersion).

FIG. 8 shows the result of Isoton II particle phase velocity measurements based on RIS recording of the response signals at 1 GHz. Virtually no dispersion is noticeable. Processing of the raw data to obtain the value of the particle velocity dispersion includes, for each current frequency value, looking for a maximum in the cross-correlation function within a 60 ns interval around the maximum obtained for the previous frequency step, i.e. obtained for one frequency increment below the frequency currently being analyzed. The maximum at the lowest frequency in the analyzed range, e.g. 1 MHz is just the absolute maximum of the cross-correlation function.

Figure 9:
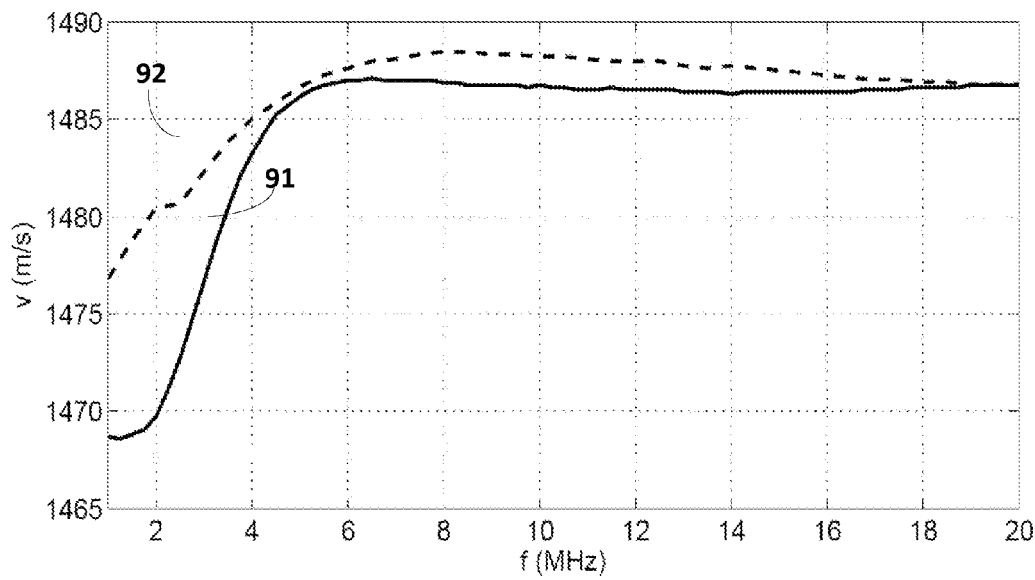
FIG. 9 shows phase velocity dispersion for a MicroMarker solution containing 4 million microbubbles/ml at two different input amplitudes: 10 mV (solid) and 50 mV (dashed).

FIG. 9 shows the calculated phase velocity dispersion for a MicroMarker solution, e.g. a contrast agent, containing 4 million bubbles/ml at two different input amplitudes: 10 mV (graph 91) and 50 mV (graph 92). The figure is in good agreement with theory in that the predicted jump in phase velocity at resonance is clearly visible. The figure also shows the influence of pressure on the bubble solution. It can be clearly seen that at pressures well above 60 kPa the shift at the resonance frequency becomes less pronounced and less steep indicating that the size distribution of the microbubbles has become wider. The resonance frequency also appears to have shifted towards a higher frequency indicating that the larger bubbles are being destroyed more rapidly. This is again in agreement with theory.

Figure 10:
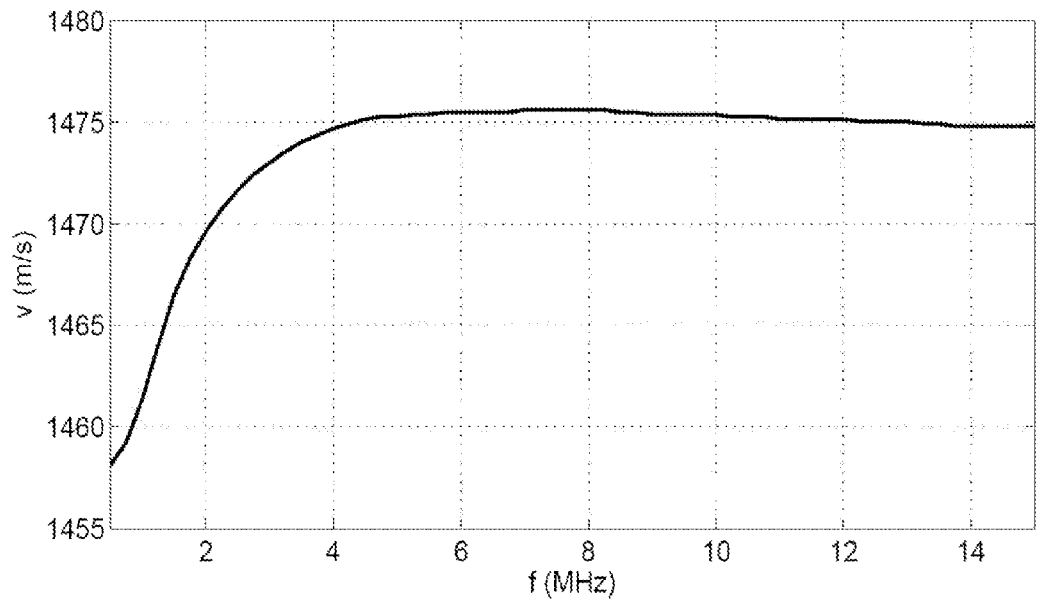
FIG. 10 shows phase velocity dispersion for a SonoVue contrast solution with a volume fraction of $4 \times 10^{-5}$.

SonoVue particle velocity dispersion measurements proved more challenging. Not only were the measurements more difficult to reproduce, the transition in phase velocity is located at lower frequencies, making measurements down to 0.5 MHz necessary. FIG. 10 shows a measurement of the phase velocity dispersion for SonoVue contrast solution with a volume fraction of $4 \times 10^{-5}$. The low resonance frequency makes detection of the entire transition difficult in the range 0.5-20 MHz with 10 MHz emitting transducers 4 and receiving transducers 7.

Figure 11:
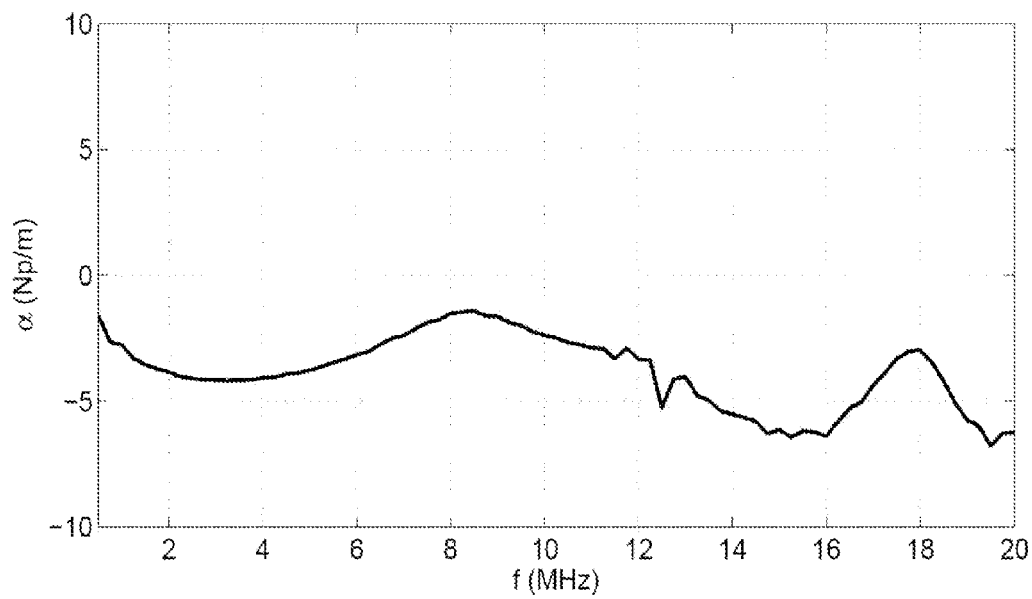
FIG. 11 shows an attenuation measurement result for Isoton II referenced to distilled water (almost no dispersion).

Determination of the attenuation by means of the reference method allowed to work without the need for knowing the transducer transfer curves or reflection coefficients that would be required using the multiple reflection method. Measurements of the attenuation rely heavily on adequately high sampling rates. For Isoton II a flat curve is expected. FIG. 11 shows an example of Isoton II attenuation dispersion with a distilled water reference. The graph clearly shows a typical form that is somewhat deviating from the expected behaviour in that it shows negative attenuation and in that it is not flat. However, compared to the high attenuation that microbubbles create, this anomaly is no cause for concern.

Figure 12:
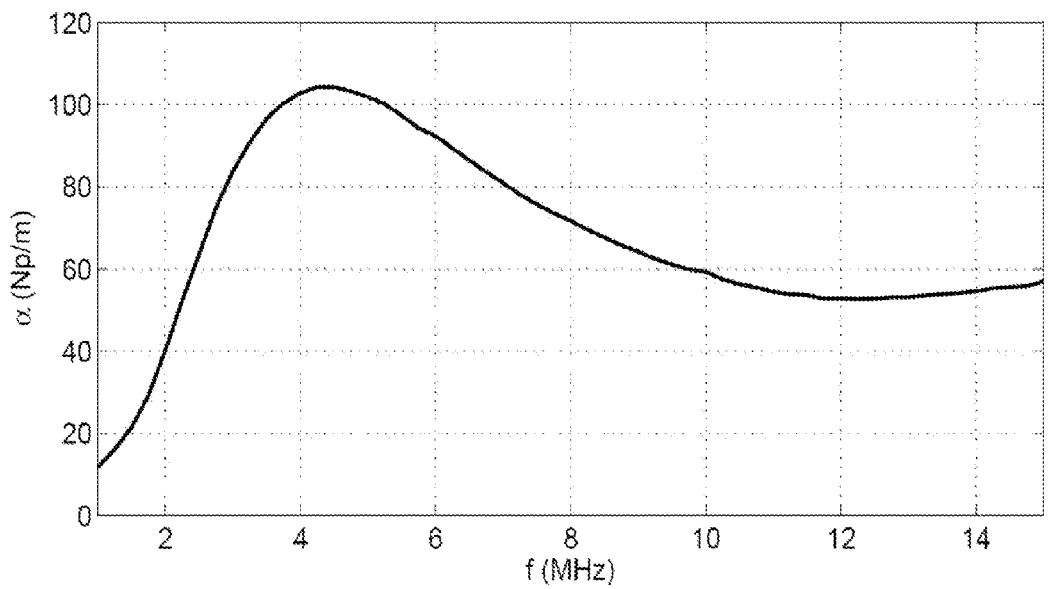
FIG. 12 shows attenuation dispersion for a MicroMarker solution containing 4 million microbubbles/ml at an input voltage of 10 mV.

Best results were obtained by using an input voltage of 10 mV for a 4 million bubbles/ml MicroMarker solution (FIG. 12). 5 mV input gave a signal that was too weak, while a 50 mV input signal resulted in destruction of part of the microbubbles.

Figure 13:
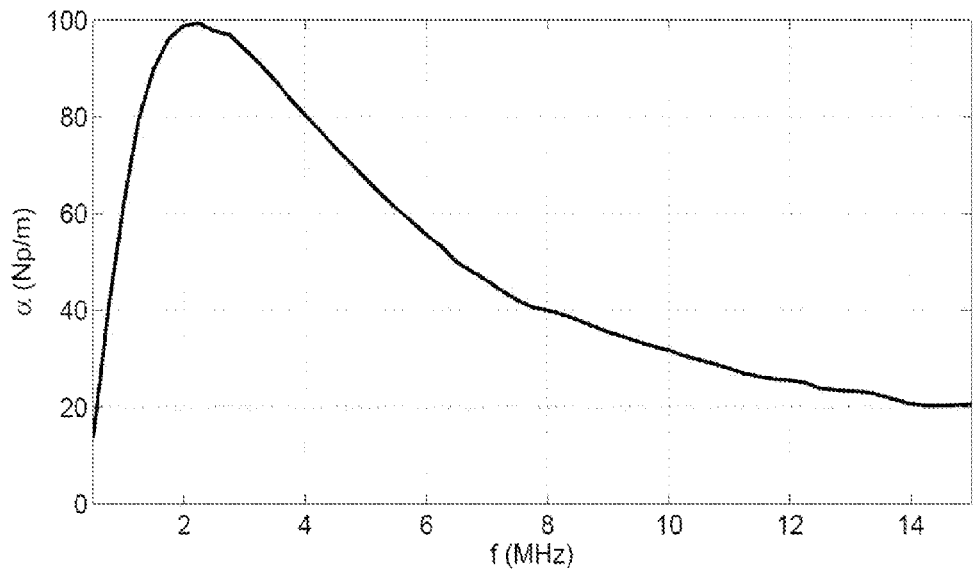
FIG. 13 shows attenuation dispersion for a SonoVue contrast solution with a volume fraction of $4 \times 10^{-5}$.

Again measurements proved more difficult with SonoVue. Not only were there significant differences in resonance frequency and attenuation between different vials, also measurements originating from the same vial proved difficult to reproduce at times. FIG. 13 shows the result of a measurement regarding attenuation on a SonoVue solution with a volume fraction of $4 \times 10^{-5}$. A clear peak can be identified at the resonance frequency of 2.25 MHz. This is, however, not always the case.

Figure 14:
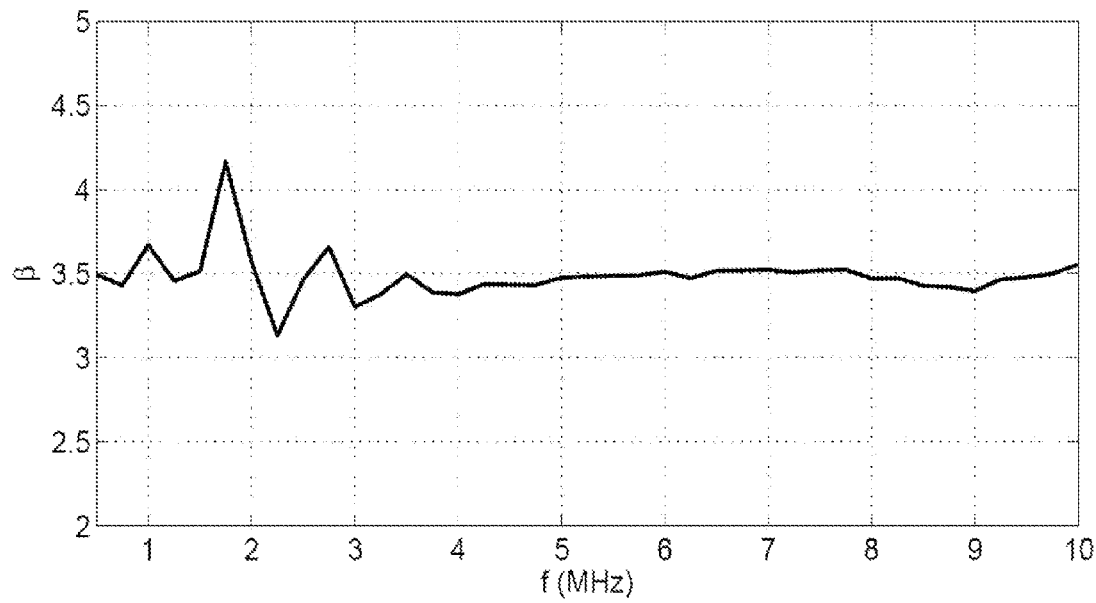
FIG. 14 shows the experimental dispersion results for the nonlinearity parameter (a) for Isoton II solution (Blackman-Nuttall window—almost no dispersion), and (b) the influence of different window functions on the appearance of the nonlinearity parameter dispersion for a MicroMarker solution containing 4 million bubbles/ml: Blackman-Nuttall (solid line), Cosine tapered (dashed line) and Hanning (dotted line).
Figure 14:
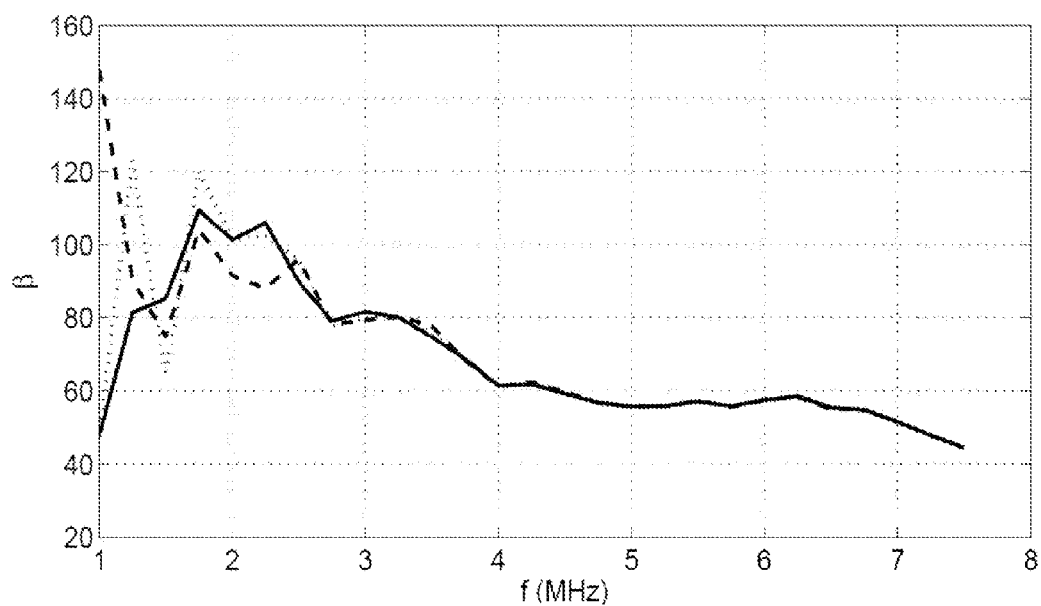

The level of nonlinearity of the liquid solution is the most difficult parameter to process. Not only does it rely on an accurate determination of the second harmonic signal, but also on correct information on the previously determined variables, namely the phase velocity and attenuation. Furthermore, the choice of window function appears to be important as is illustrated in FIG. 14(*b*) which illustrates the dependence of nonlinearity dispersion on window function. In most cases the Blackman-Nuttall window seems to produce the smoothest curves. It is however worth noting that all windows do indicate a large rise in the nonlinearity parameter dispersion in the lower frequency range, consistent with theory. The nonlinear parameter of the Isoton II reference, as determined by measuring relative to water, can be used to help with the final window choice. Good measurements keep the nonlinearity parameter of Isoton II nearly constant at 3.5-3.6 (FIG. 14 (*a*)).

Figure 15:
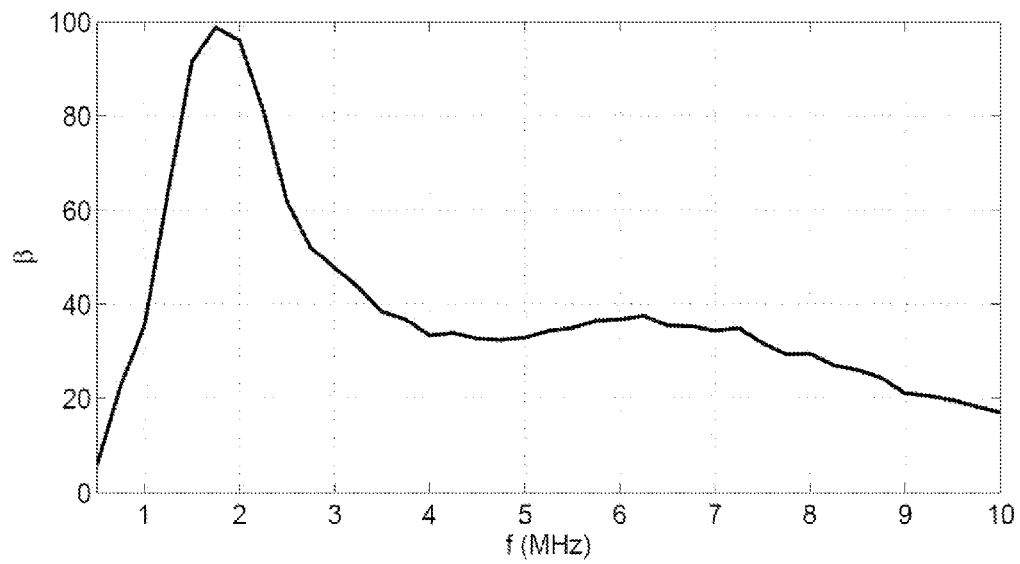
FIG. 15 shows the experimental dispersion results for the nonlinearity parameter for a MicroMarker solution containing 4 million microbubbles/ml.

FIG. 15 shows the nonlinearity parameter dispersion for a MicroMarker solution of 4 million bubbles/ml. The resonance frequency is around 5.5 MHz. The peak in nonlinearity is situated at 1.75 MHz. This is considerably lower than half the resonance frequency. The figure also shows a secondary smaller peak at frequencies higher than the resonance frequency.

Figure 16:
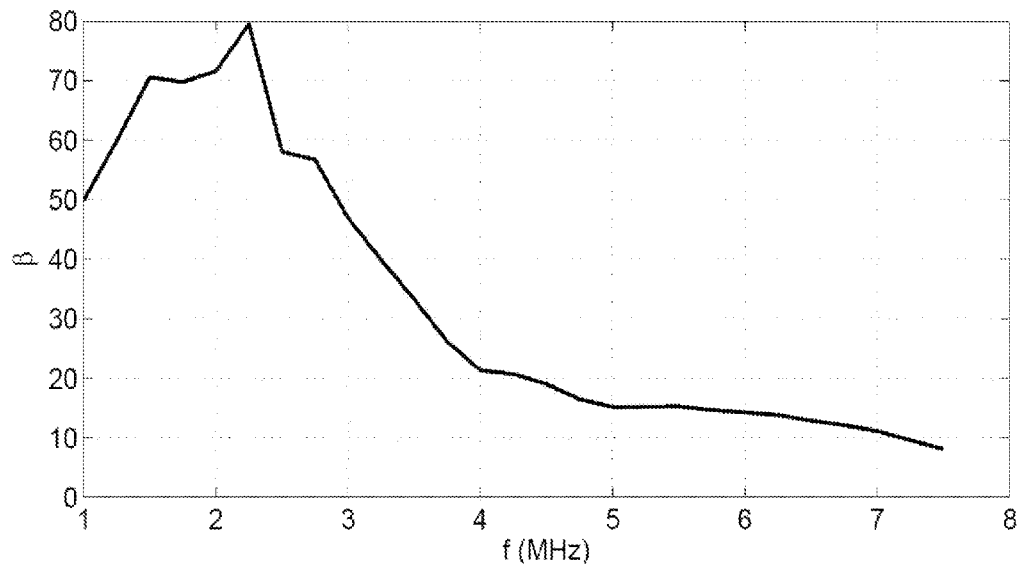
FIG. 16 shows the experimental dispersion results for the nonlinearity parameter for a SonoVue contrast solution with a volume fraction of $4 \times 10^{-5}$.

A curve for the nonlinearity parameter of a SonoVue solution with a volume fraction of $4 \times 10^{-5}$ is given in FIG. 16. This graph is less smooth than the graph for MicroMarker. This can be related to the more difficult measurements of the phase velocity and attenuation.

It is clear from the above that the nonlinearity parameter is influenced by the presence of bubbles 3, as it shows very high values at frequencies half the resonance frequency or lower.

Figure 17:
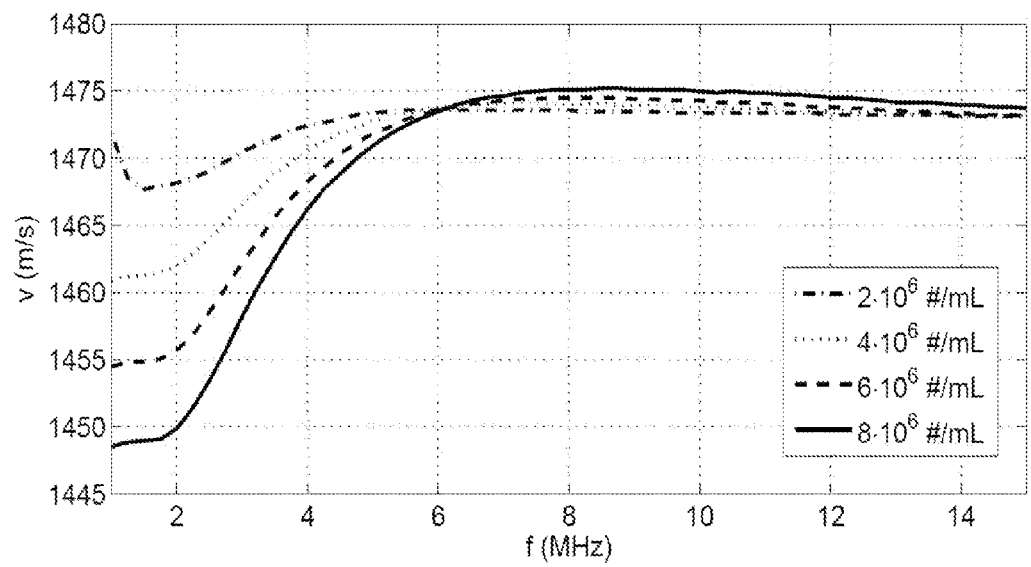
FIG. 17 shows phase velocity dispersion measurements (a) and attenuation dispersion measurements (b) for different concentrations of a MicroMarker solution ranging from 2 to 8 million bubbles/ml.
Figure 17:
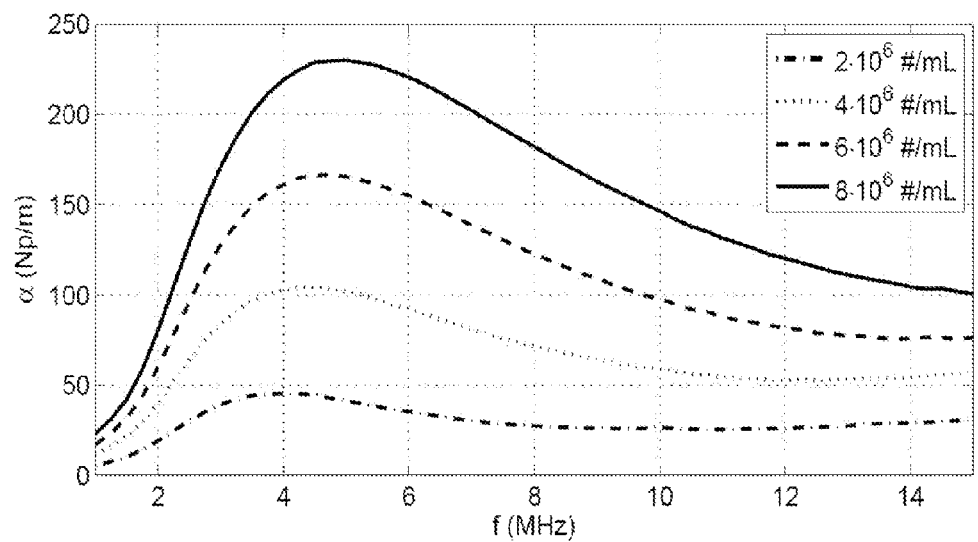

Thus far only one microbubble concentration has been studied: 4 million bubbles/ml or $4.10^{-5}$ volume fraction for MicroMarker and SonoVue, respectively. Concentrations in these orders of magnitude are indeed common in medical applications. Contrast is typically injected in higher concentrations that are diluted to these levels in the blood. The concentration that is needed depends on the target anatomy: well vascularised tissues such as the kidney and liver require lower bubble concentrations than tumors and muscles. Because of this differentiation an investigation of the influence of concentration on the ultrasonic properties imposes itself. Concentrations between 1 and 10 million microbubbles/ml or between $1.10^{-5}$ and $1.10^{-4}$ are of interest. FIG. 17 shows the influence of concentration of MikroMarker microbubbles (illustrated as #/ml in FIG. 17) on the linear parameters: phase velocity dispersion and attenuation dispersion. The concentrations used for the graphs range from 2 to 8 million bubbles/ml. The phase velocity and attenuation dispersion seem to scale linearly with concentration. In terms of the typical dispersion characteristics, a doubling concentration results in a phase velocity jump at resonance that is twice as large and a maximal attenuation that is twice as high. Another observation is the gradual shift in resonance frequency, when comparing different concentrations.

Figure 18:
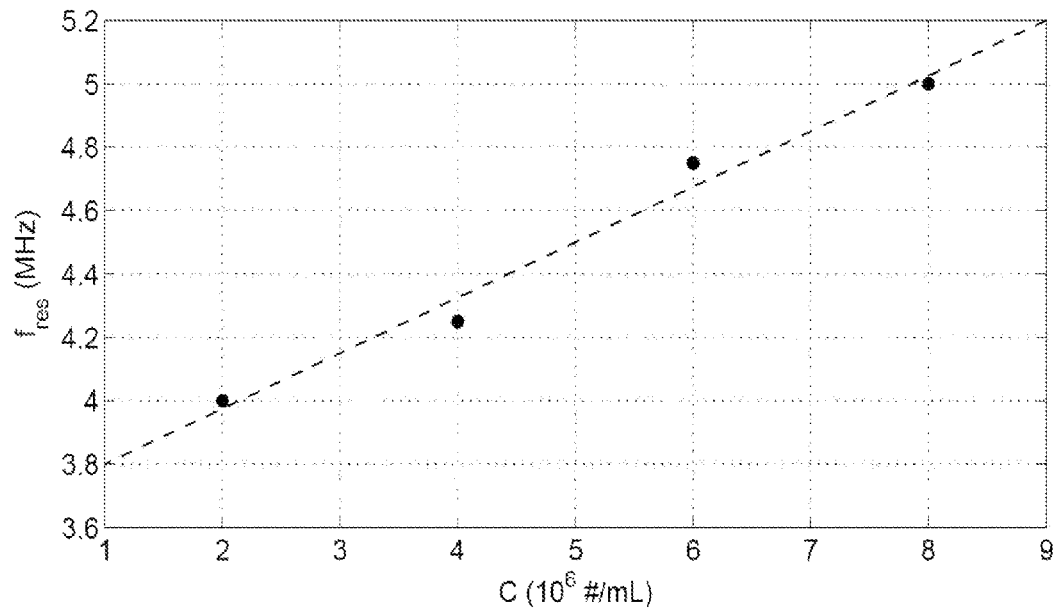
FIG. 18 shows the shift in resonance frequency as a function of the microbubble concentration for a MicroMarker solution.

FIG. 18 pictures the resonance frequency as a function of the microbubble concentration (illustrated in $10^6$ #bubbles/ml) and thus illustrates the influence of microbubble concentration on the resonance frequency. A linear rise in the frequency is noticeable. However, the rise is fairly small (from 4 MHz to 5 MHz for a factor four increase in bubble concentration), especially when compared to the step size (0.25 MHz). Looking back at simulations from theory, there is indeed a prediction of a comparable shift in resonance frequency with increased concentration of bubbles. The dashed line illustrates a linear fit through the data points.

Figure 20:
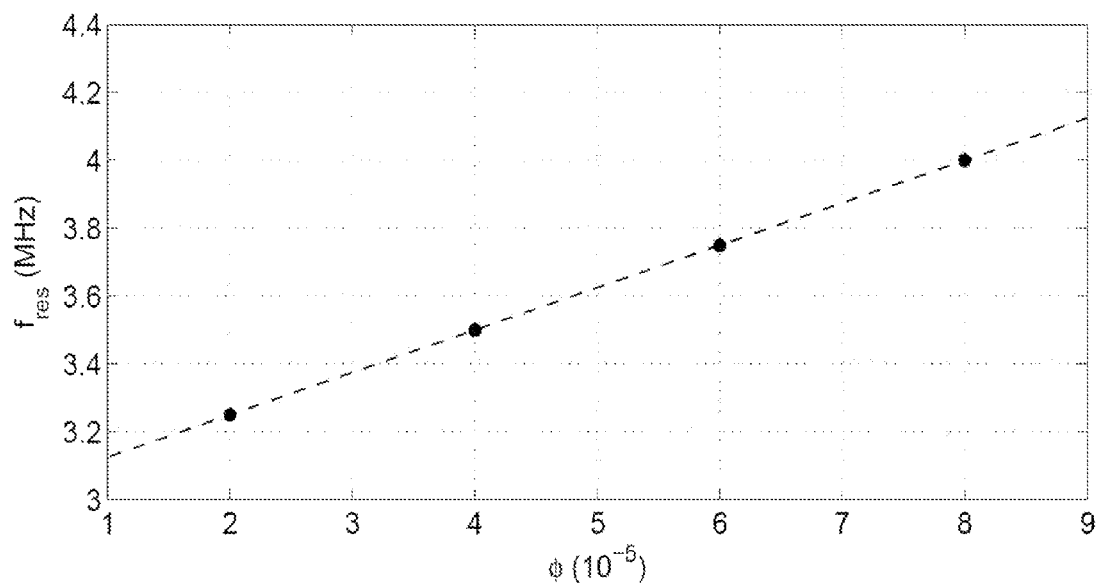
FIG. 20 shows the shift in the resonance frequency as a function of the microbubble concentration for a SonoVue contrast solution.
Figure 19:
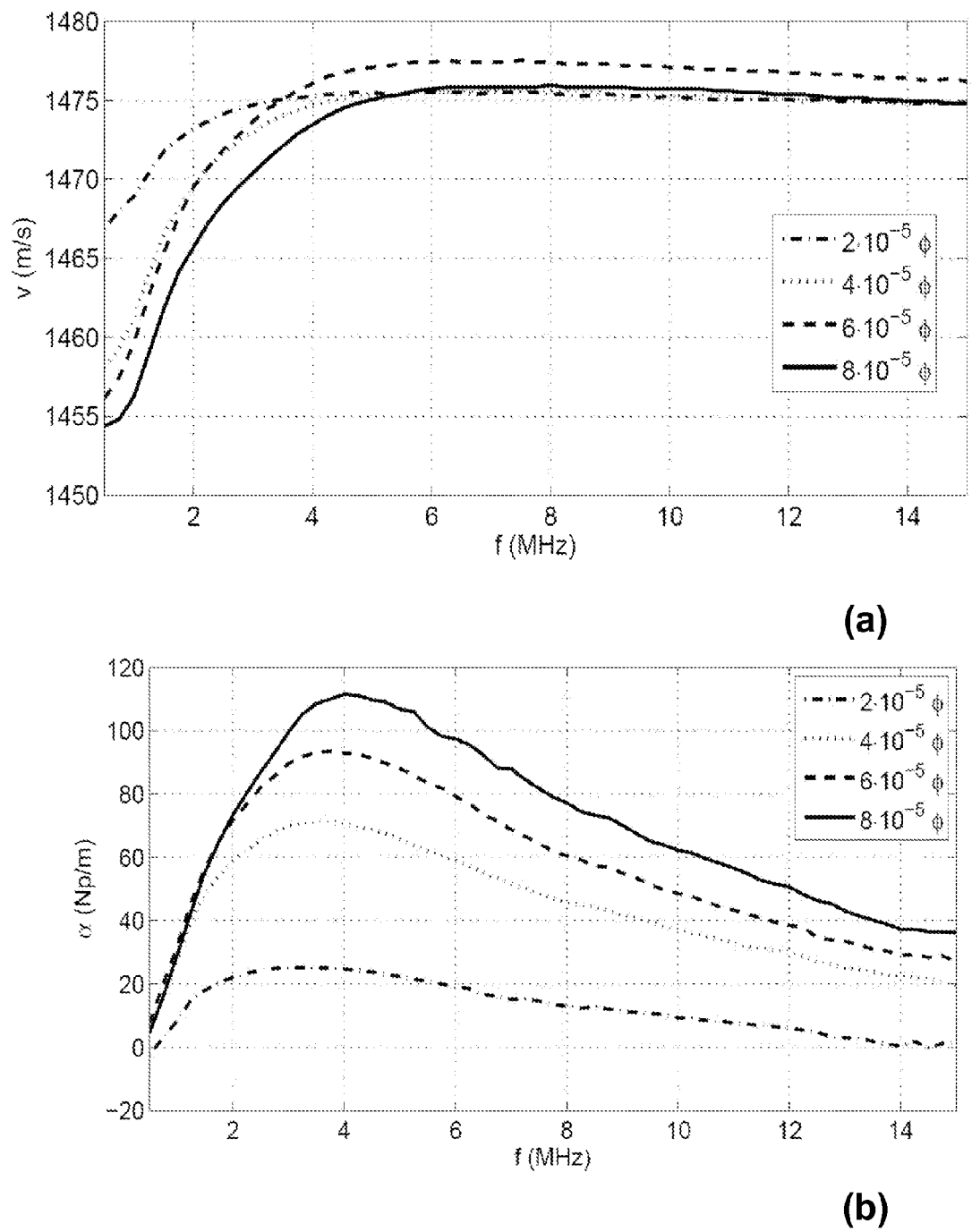
FIG. 19 shows phase velocity dispersion measurements (a) and attenuation dispersion measurements (b) for different concentrations of a SonoVue contrast solution, ranging from $2 \times 10^{-5}$ to $8 \times 10^{-5}$ volume fraction.

For SonoVue microbubbles, results are given in FIG. 19, showing the influence of concentration on the linear parameters: phase velocity dispersion and attenuation dispersion. More specifically FIG. 19 (*a*) shows the phase velocity for different concentrations of SonoVue contrast solutions, whereas FIG. 19 (*b*) illustrates attenuation for difference concentrations of SonoVue contrast solutions. The concentrations of SonoVue contrast solutions used for the graphs range from $2 \times 10^{-5}$ volume fraction to $8 \times 10^{-5}$ volume fraction, indicated as φ on the graphs. The results are similar to those for MicroMarker solutions (compare FIG. 17). The different properties again seem to scale quite good with concentration. Again a linear rise in resonance frequency can be distinguished and this is represented in FIG. 20, which illustrates the influence of the volume fraction on resonance frequency when using SonoVue microbubbles and wherein the dashed line illustrates the linear fit of the data points. The fact that this shift in resonance frequency occurs for both available contrast agents suggests that the shift is indeed significant.

The measuring procedure for unradiated samples, presented hereabove, was developed to eliminate potential time effects. Even in a closed vial, time will induce changes. Diffusion will take place, limiting the usage of a reconstituted vial to a few hours. In order to study radiation effects, it is therefore recommended that every measurement is rectified with a time correction. This time correction was achieved by dedicating a vial to measurements in which time was monitored meticulously. Falling back on observations from simulations, three typical dispersion characteristics were monitored in time. For the phase velocity the magnitude of the jump at resonance was studied, for the attenuation and nonlinearity parameter the maximum of the peak was of interest. This resulted in the graphs presented in FIG. 4, wherein the line represents the linear fit of the data points.

The graphs show a linear drop in all three parameters and the linear fits are represented as lines 41, 42, 43. For the phase velocity jump the fit y=ax+b reads:

$$a_{PV} = -0.038 \pm 0.005$$

$$b_{PV} = 28.45 \pm 0.7$$

where b is actually not important since this value will differ from vial to vial. For the attenuation drop the parameters of the linear fit are:

$$a_{At} = -0.33 \pm 0.05$$

$$b_{At} = 244.42 \pm 7.00$$

while for the nonlinearity parameter the parameters are:

$$a_{NL} = -0.11 \pm 0.01$$

$$B_{NL} = 112.85 \pm 2.00$$

The somewhat large deviations from the fitted lines can be attributed to the fact that no averaging over different samples at the same moment in time has taken place. This immediately shows the importance of such averaging if one is to discover deviations from the normal diffusion behaviour.

Measurement Procedure with Irradiation

In order to investigate the influence of ionizing radiation, irradiations were carried out at the Studie Centrum voor Kernenergie (SCK•CEN) in Mol, Belgium. Samples could be irradiated with a 250 kV RX-machine capable of delivering dose rates up to 0.7 Gy/min at the Calibration department and with gamma rays produced from spent fuel of the Belgian Reactor 2 (BR2) where dose rates up to 10 Gy/min could be achieved. Irradiations were always conducted upon the original reconstituted vials. The experiment with the high dose rate Co source (i.e. 10 Gy/min), in the BR2, was planned in order to minimize the effect of time on the evolution of the properties of the microbubbles, ensuring the best possible control on the stability of the contrast agent.

A step by step guide to ensure reproducible results of experiments on ultrasonic contrast agents aimed at understanding the possible influence of ionizing radiation is presented here. Again, a "single measurement" comprises the recording of the response signals in the frequency range 0.5-20 MHz in steps of 0.25 MHz. When compared to the set of reference signals, each single measurement allows a determination of the experimental phase velocity, attenuation and nonlinearity dispersion relations. However, for the specific goal of testing irradiated bubbly liquids a somewhat adapted measurement sequence is required:

1. The sample holder 21 is filled with a predetermined amount of a reference liquid such as distilled water (e.g. 15 ml). An energy wave 5 is emitted to the sample in the sample holder 21, and a response signal 6 is determined. A single measurement is taken without determination of phase velocity, attenuation or nonlinearity parameter.

2. The sample holder 21 is emptied and filled with a predetermined amount of diluents such as a saline solution, e.g. Isoton II (0.9% NaCl in distilled water) solution, which contains a phosphate buffer, e.g. 15 ml. A single measurement is taken for the pure saline solution and the phase velocity, attenuation and nonlinearity are determined by the reference method. Distilled water is taken as reference.
3. A vial of an ultrasonic contrast agent is prepared. As an example, MicroMarker Contrast Agent, comprising a white powder, may be reconstituted by injecting 1 ml of diluents such as Isoton II in the vial. Then the vial is vented and gently agitated for a predetermined time period, for example 1 minute. Afterwards the solution needs to rest for a while, for example ten minutes. At this point the concentration of the solution in the example described is $2.10^9$ microbubbles/ml.
4. A small amount of ultrasonic contrast agent, e.g. MicroMarker solution, is taken from the vial, for example by means of a syringe with needle, and is put into a recipient, for example an Eppendorf tube.
5. From this recipient, e.g. Eppendorf tube, a predetermined volume, e.g. a volume of 30 microliter, is pipetted into the predetermined amount, e.g. 15 ml of diluents, e.g. Isoton II, in the sample holder 21, resulting, for the example described, in a final concentration of $4.10^6$ microbubbles/ml. A single measurement is taken with the Isoton II measurement (step 2) as reference. Afterwards the sample holder 21 is emptied and cleaned, e.g. washed with distilled water. The sample holder 21 is refilled with a predetermined amount, e.g. 15 ml, of diluent, e.g. Isoton II.
6. Step 4 and 5 may be repeated twice to ensure repeatability and to be able to take averages.
7. The reconstituted vial of ultrasonic contrast agent, e.g. of MicroMarker, is irradiated with ionizing radiation, and a certain dose is delivered to the bubbles in the vial.
8. Step 4, 5 and 6 are repeated.
9. Step 7 and 8 are repeated for the desired concentration yielding information on the influence of different doses on the ultrasonic properties of the microbubbles.

Results: Measurements after Irradiation

Two irradiation aspects determine the influence of ionizing radiation on the samples. First there is of course the dose, which is the amount of radiation that the sample actually receives, expressed in Gray (Gy). The dose rate, on the other hand, is a measure of the rate at which the radiation is delivered to the sample. Both of these aspects were investigated. As in the case of non-radiated samples, four aspects of the ultrasonic dispersive behaviour were studied: the jump in phase velocity at resonance, the evolution of the maximal attenuation at resonance, the maximal nonlinear parameter and the possible shift in resonance frequency. Below, only results for MicroMarker contrast agents are given, the present invention, however, not being limited thereto. The table herebelow gives an overview of the different MicroMarker vials that were tested and the type of ionizing radiation they were irradiated with.

| Vial Number | Doses (Gy) | Type | Dose rate (Gy/min) | Symbol |
|---|---|---|---|---|
| 1 | 5; 15; 40 | X-ray | 0.7 | Circle |
| 2 | 65; 85 | X-ray | 0.7 | Square |
| 3 | 50; 90; 190 | γ-ray | 10 | Diamond |
| 4 | 20; 40; 60 | γ-ray | 10 | Triangle |

The most straightforward information that can be immediately drawn from the velocity dispersion is the magnitude of the jump at resonance. Since this jump varies in time as well, the measured values are always time corrected. FIG. 5(*a*) shows the time-corrected results that were obtained for different vials and normalized to the reference measurements at 0 Gy. In the presented figure a clear dependence of the jump in the phase velocity at resonance to the administered dose can be noticed.

FIG. 5(*b*) gives an overview of the maximal attenuation measurements that were conducted on four different vials. The maximal attenuation value is normalized to the reference at 0 Gy. Low dose rate measurements, of 0.7 Gy/min, (circles and squares show rather good linear relationships between dose and maximal attenuation. Likewise, experiments conducted on two different vials at BR2 with high dose rates, of 10 Gy/min, (triangle and diamond) also are showing a clear linear relationship.

As already discussed, the nonlinearity parameter is strongly dependent on the choice of the window. It is therefore difficult to compare results from different vials. FIG. 5(*c*) shows the results of the analysis of the dose dependence of the maximal nonlinearity parameter. A clear influence on the ionizing radiation is again visible. However, this time the results are not pointing towards a linear relationship. The presented measurements indicate a sharp rise for doses up to 20 Gy, followed by a plateau and less steep rise for higher doses.

Discussion

The examples presented above give a clear indication that ionizing radiation affects the ultrasound contrast agent, e.g. the MicroMarker bubbles, in a strong enough manner to change their ultrasonic properties without fully destroying the contrast in the diluents, e.g. Isoton II solution. This observation supports the feasibility of possible in-vivo dosimetry.

As a first step towards quantification of the affected bubble parameters by ionization, the link between the model of Hoff as known from L. Hoff, "Acoustic characterization of contrast agents for medical ultrasound imaging," Ph.D. thesis, Norwegian University of Science and Technology, 2000, and the experiments without radiation is investigated by an inverse nonlinear least squares fitting model.

A fit between experiment and theory provides information on the values of the parameters of the theoretical model. This can be done using for example standard Matlab routines such as lsqcurvefit. Due to the high number of parameters the fitting procedure can be tackled in different ways. First the focus will be on retrieving parameters for the size distribution of the ultrasound contrast agent, e.g. the MicroMarker contrast agents.

Figure 21:
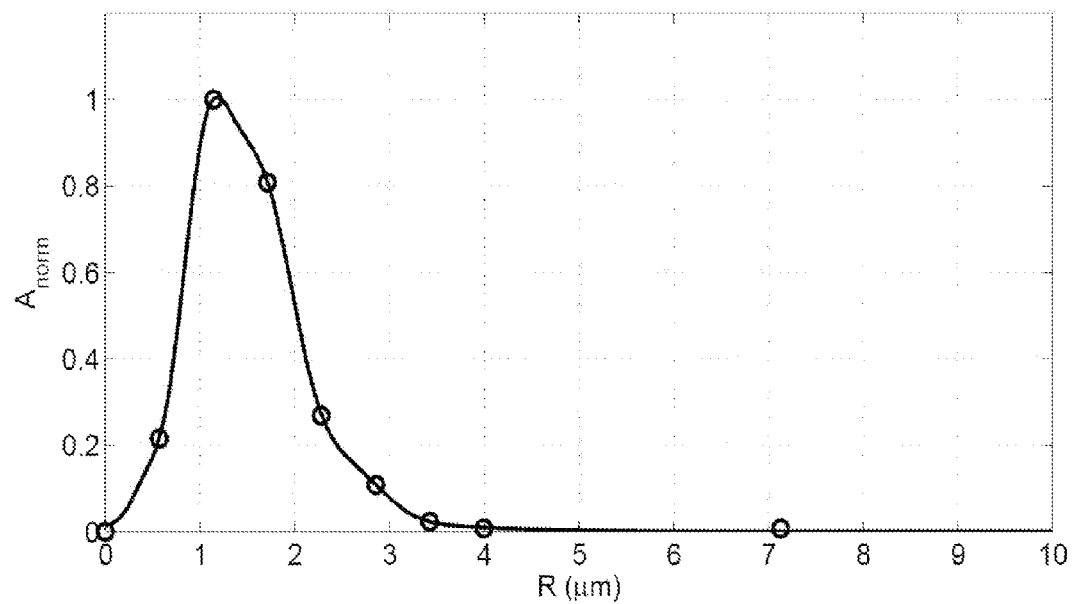
FIG. 21 shows a plot of a normalized discrete experimental size distribution that was interpolated with the function interp1 in Matlab according to a shape-preserving piecewise cubic interpolation.

A discrete experimental size distribution was obtained from analysis of microscopic images as previously described. In order to obtain an analytical approximation the data were normalized and then interpolated, for example with the intrinsic Matlab function interp1 with option 'pchip' which stands for shape-preserving piecewise cubic interpolation. The thus interpolated curve is shown in FIG. 21 which shows the normalized amplitude in function of the radius.

Figure 22:
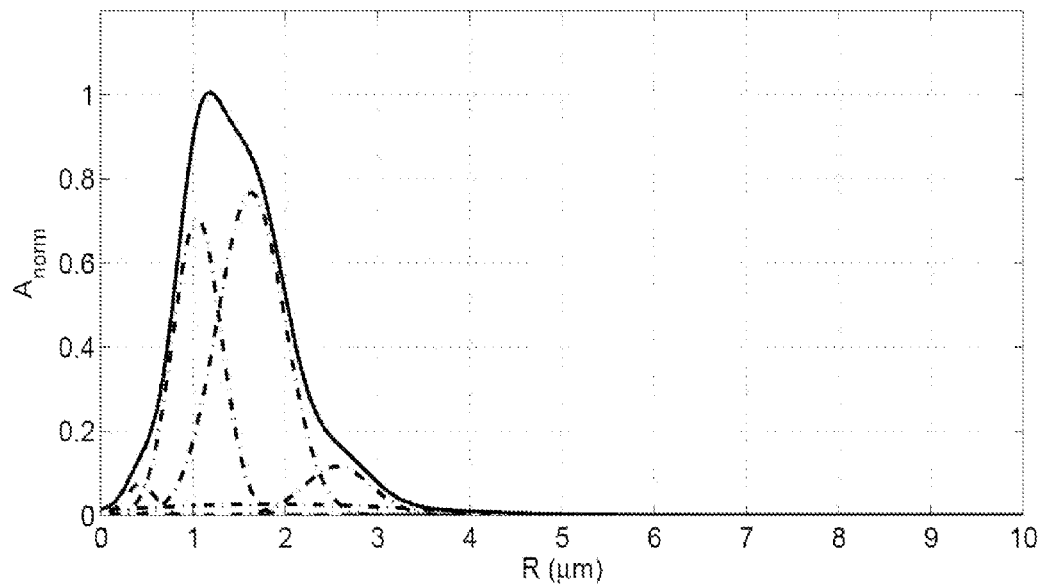
FIG. 22 shows a plot of 5 different Gaussian functions (dash-dotted line) that were used to approximate the experimental size distributions, the resulting sum (solid line) provides a good approximation of the actual curve.

The next step is to transform the interpolated data to a Gaussian mixture model fit, e.g. a sum of 5 Gaussian functions. This means that a parameter fit needs to be carried out to find 15 different parameters, 3 (the centre radius, the width and the relative height) for each Gaussian function. In order to achieve this fit a nonlinear inversion has to be conducted. This may for example be done in Matlab by using the routine lsqcurvefit. The table herebelow shows the 15 parameters that were obtained, while FIG. 22 (illustrating the normalized amplitude in function of the radius) shows the results of the fitting, displaying the five individual Gaussians and their sum which appears to be a very good approximation of the interpolated curve.

| Radius | Width | Rel. Ampl. |
|---|---|---|
| 0.4273 | 0.1549 | 0.0292 |
| 1.0459 | 0.2622 | 0.4638 |
| 1.6303 | 0.3678 | 0.7068 |
| 2.5683 | 0.3659 | 0.1065 |
| 1.8422 | 1.4663 | 0.1000 |

Figure 23:
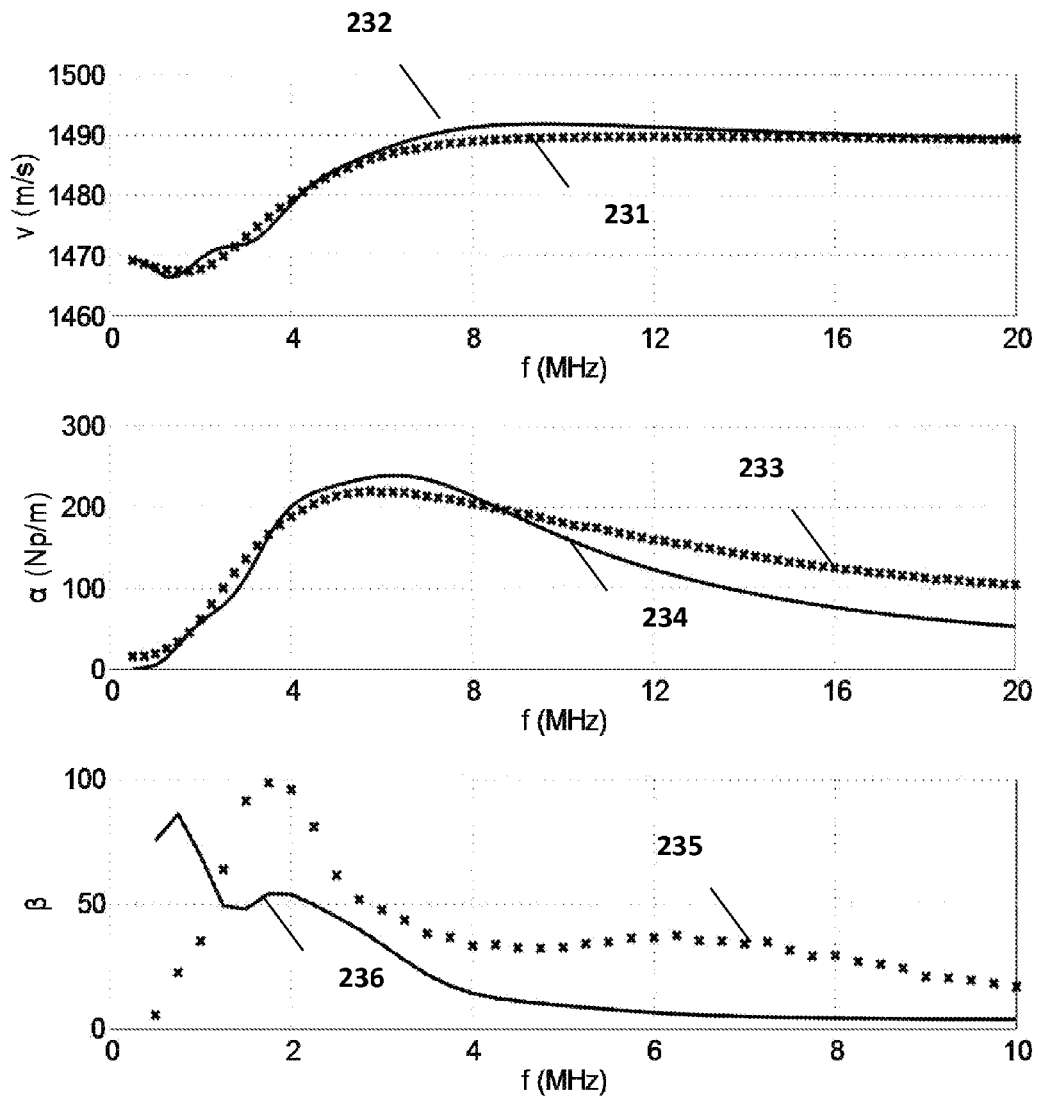
FIG. 23 shows a plot of the experimentally achieved phase velocity, attenuation and nonlinearity parameter (circles) dispersions versus the numerically determined dispersions calculated with Hoffs model by insertion of fitted parameters (solid line).

With the size distribution determined analytically the ultrasonic dispersion graphs can be fitted using a four parameter fitting procedure with the following parameters: $G_S \cdot d_{S0}$, $\eta_S \cdot d_{S0}$ (the independent combinations of the parameters from Hoffs model), $\gamma$ the surface tension and a parameter that can rescale the size distribution. The other variables, e.g. those related to the liquid medium or diffusion coefficients, are considered to be fixed and known. As an example, data from a measurement at 0 Gy were subjected to the fitting procedure. The nonlinear least squares fit of the phase velocity, attenuation and nonlinear coefficient results in the following values for the fitted parameters: $G_S \cdot d_{S0} = 1.108$, $\eta_S \cdot d_{S0} = 8.557 \cdot 10^9$, $\gamma = 0.0$ and the normalization constant for the distribution is equal to $1.554 \cdot 10^{12}$. The results of the fitting are shown in FIG. 23. Graphs 231, 233 and 235 illustrate experimentally achieved values, and graphs 232, 234 and 236 illustrate corresponding fits.

The graphs can be analyzed as follows. The fits 232, 234, for the attenuation (a) and phase velocity (V) are good, but not perfect. The attenuation suffers from a bad approximation at higher frequencies. It is to be recalled that the size distribution was determined from an analysis of microscopic images. An inherent problem with the microscopy technique for determining the size distribution is the inability to detect very small bubbles. An underestimation of the small bubbles that have high resonance frequencies could explain this discrepancy. The fit 236 for the nonlinearity parameter ($\beta$) dispersion shows the largest deviation from the measured values 235. Again the higher frequencies are underestimated while the extra peak at very low frequencies was not observed in experiments. This may be attributed to the low signal amplitudes (especially for the second harmonic) in the lower frequency range that are a result from the fact that 10 MHz transducers 4, 7 were employed for emission and reception.

Conclusion

Radiation experiments showed that ionizing radiation affects the elastic properties of ultrasonic contrast agents, more specifically the elastic properties of the encapsulated gas-filled microbubbles. Preferably, the encapsulated gas-filled microbubbles are bubbles which can produce an echo for reception and analysis, to afford imaging of a region. This is evidenced by a measurable alteration of three basic ultrasonic dispersion parameters using an ultrasonic based read-out system (8,4,7): phase velocity, attenuation and nonlinearity. Increasing doses resulted in an increasing maximal attenuation, an increasing maximal nonlinearity and an increasing magnitude of the jump in the phase velocity. Hence determination of phase velocity, attenuation, and/or nonlinearity dispersion characteristics of microbubbles 3 in contrast agents 2 may be used for determining radiation dose.

It is to be understood that the present invention is not limited to the particular features of the means and/or the process steps of the methods described as such means and methods may vary. It is also to be understood that the terminology used herein is for purposes of describing particular embodiments only, and is not intended to be limiting. It is also to be understood that plural forms include singular and/or plural referents unless the context clearly dictates otherwise. It is moreover to be understood that, in case parameter ranges are given which are delimited by numeric values, the ranges are deemed to include these limitation values.

The above description is for the purpose of teaching the person of ordinary skill in the art how to practice the present invention, and it is not intended to detail all those obvious modifications and variations thereof which will become apparent to the skilled reader upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

The invention claimed is:

1. A system for measuring radiation dose, the system comprising:
    an excitation device adapted for directing an energy wave at a volume of a substance comprising gas-filled microparticles, which volume has been exposed to ionizing radiation;
    a detector for detecting a response signal emitted and/or modified from the volume of the substance comprising gas-filled microparticles; and
    a control unit, wherein the control unit is adapted for calculating, based on the response signal, a dose of ionizing radiation received by the volume of the substance.

2. A system according to claim 1, wherein the control unit is adapted for calculating a dose of ionizing radiation received by the volume of the substance, taking into account a change of elasticity of the gas-filled microparticles.

3. A system according to claim 1, wherein the excitation device comprises an ultrasound or electromagnetic (RF) transducer and the detector is adapted for acquiring an ultrasonic or electromagnetic (RF) response signal from the volume of the substance comprising encapsulated gas-filled microparticles.

4. A system according to claim 1, wherein the control unit is adapted for determining a spatial distribution of the received dose of ionizing radiation.

5. A system according to claim 1, wherein the control unit is adapted for calculating, during radiotherapy, a dose of ionizing radiation received by said volume of the substance.

6. A system according to claim 1, wherein the control unit is adapted for calculating, during radiotherapy, a dose of ionizing radiation received by a patient having said volume of the substance administered.

7. A system according to claim 1, whereby the control unit is adapted for calculating a dose of ionizing radiation received by the volume of the substance, taking into account a change of physical properties or chemical properties or a combination of physical and chemical properties of the gas-filled microparticles due to interaction with the dose of ionizing radiation.

8. A system according to claim 7, wherein the control unit is adapted for calculating a dose of ionizing radiation received by the volume of the substance, taking into account a change of one or more physical properties of said encapsulated gas-filled microparticles selected from the group consisting of radius, size distribution, number of particles, shell thickness, shear modulus, shear viscosity, and surface tension.

9. A system according claim 1, wherein the excitation device is adapted for keeping the encapsulated gas-filled microparticles intact when directing the energy wave at the volume of the substance comprising gas-filled microparticles.

10. A system according to claim 1, wherein the control unit is adapted for controlling the set-up and parameters for the detector.

11. A method for measuring a received dose of ionizing radiation, the method comprising:
    directing an energy wave at a volume of a substance comprising gas-filled microparticles, whereby said volume of the substance is previously exposed to ionizing radiation;
    detecting a response signal from the volume; and
    determining the radiation dose received by the volume during the ionizing radiation exposure, taking into account the detected response signal.

12. A method according to claim 11, wherein detecting a response signal comprises detecting an interaction between the ionizing radiation and said volume of the substance.

13. A method according to claim 12, further comprising quantifying said detected interaction by analyzing a dispersive response of the volume in function of the received dose of ionizing radiation.

14. A method according to claim 13, wherein analyzing said dispersive response comprises analyzing dispersive characteristics of parameters of said encapsulated gas-filled microparticles in function of the dose of ionizing radiation.

15. A method according to claim 11, further comprising a time correcting method including:
    directing an energy wave at a volume of the substance comprising functionalized gas-filled microparticles whereby said volume is not exposed to ionizing radiation;
    detecting a response signal from the volume;
    determining a time correction value taking into account said detected response signal;
    applying said time correction value to a detected response signal, said response signal determined on a volume previously exposed to ionizing radiation.

16. A method according to claim 11, wherein directing an energy wave at the volume of the substance comprises emitting an ultrasonic or RF wave and detecting a response signal comprises detecting an ultrasonic or RF response signal.

17. A method according to claim 11, wherein determining the radiation dose includes determining a spatial distribution of the radiation dose.

18. A method according to claim 11, further comprising determining, during radiotherapy, the radiation dose received by the volume of the substance.

19. A computer program product for, if implemented on a control unit, performing a method according to claim 11.

* * * * *